(12) United States Patent
Marx

(10) Patent No.: US 9,791,433 B2
(45) Date of Patent: Oct. 17, 2017

(54) MULTI-ORGAN CHIP WITH IMPROVED LIFE TIME AND HOMOEOSTASIS

(71) Applicant: TissUse GmbH, Berlin (DE)

(72) Inventor: Uwe Marx, Spreenhagen bei Berlin Brandenburg (DE)

(73) Assignee: TISSUSE GMBH, Spreenhagen (DE)

( * ) Notice: Subject to any disclaimer, the term of this patent is extended or adjusted under 35 U.S.C. 154(b) by 170 days.

(21) Appl. No.: 14/431,661

(22) PCT Filed: Aug. 15, 2013

(86) PCT No.: PCT/EP2013/067073
§ 371 (c)(1),
(2) Date: Mar. 26, 2015

(87) PCT Pub. No.: WO2014/048637
PCT Pub. Date: Apr. 3, 2014

(65) Prior Publication Data
US 2015/0253309 A1    Sep. 10, 2015

Related U.S. Application Data

(60) Provisional application No. 61/706,928, filed on Sep. 28, 2012.

(30) Foreign Application Priority Data

Sep. 28, 2012  (EP) .................................... 12186550

(51) Int. Cl.
*G01N 33/50* (2006.01)
*B01L 3/00* (2006.01)
(Continued)

(52) U.S. Cl.
CPC .... *G01N 33/5088* (2013.01); *B01L 3/502746* (2013.01); *B01L 3/502761* (2013.01);
(Continued)

(58) Field of Classification Search
CPC ..... B01L 2300/0816; B01L 2400/0481; B01L 2400/0655; B01L 2400/082;
(Continued)

(56) References Cited

U.S. PATENT DOCUMENTS

| 2009/0191631 | A1  | 7/2009 | Bornemann |
| 2011/0086382 | A1* | 4/2011 | Marx ................ B01L 3/502761 435/29 |
| 2012/0214189 | A1* | 8/2012 | Shuler ................... C12M 23/16 435/29 |

FOREIGN PATENT DOCUMENTS

| WO | WO-2008/024855 A1 | 2/2008 |
| WO | WO-2009/146911 A2 | 12/2009 |
| WO | WO-2012/016711 A1 | 2/2012 |

OTHER PUBLICATIONS

International Search Report for PCT/EP2013/067073, ISA/EP, Rijswijk, NL dated Oct. 9, 2013.

\* cited by examiner

*Primary Examiner* — Nathan Bowers
*Assistant Examiner* — Lydia Edwards
(74) *Attorney, Agent, or Firm* — Harness, Dickey & Pierce, P.L.C.

(57) ABSTRACT

The present invention is directed to a multi-organ-chip device comprising a base layer; an organ layer arranged on the base layer; an antra layer arranged on the organ layer; and an actuator layer; wherein the base layer is configured to provide a solid support for the further layers; the organ layer is configured to comprise a multiplicity of individual organ equivalents, each organ equivalent comprising one or more organ growth sections, each of the organ growth sections being configured to comprise an organoid cavity for housing at least one organoid of an organ and to comprise a micro-inlet and a micro-outlet for fluid communication (Continued)

between the organoid cavity of the organ growth section and a self-contained circulation system, wherein the organ layer comprises at least one organ equivalent configured to represent the organs lung, small intestine, spleen, pancreas, liver, kidney and bone marrow, respectively, and a self-contained circulation system configured to be in direct fluid communication with the organ growth sections of the organ layer via the micro inlets and outlets of the organ growth sections; the antra layer is configured to comprise a multiplicity of cavities and tubes arranged to be in fluid communication with selected organ equivalents or organ growth sections in order to allow for exchange of fluids between cavities and organ growth sections; and the actuator layer is configured to comprise a multiplicity of actuators arranged and configured to regulate a pressure force applied on a selected organ equivalent, the self-contained circulation system and/or part thereof.

19 Claims, 9 Drawing Sheets

(51) Int. Cl.
*C12M 3/06* (2006.01)
*C12M 1/04* (2006.01)
*C12M 1/00* (2006.01)
*C12M 1/34* (2006.01)
*C12M 3/00* (2006.01)
*C12M 1/12* (2006.01)
*C12M 1/02* (2006.01)

(52) U.S. Cl.
CPC ............ *C12M 21/08* (2013.01); *C12M 23/04* (2013.01); *C12M 23/16* (2013.01); *C12M 23/24* (2013.01); *C12M 23/40* (2013.01); *C12M 23/48* (2013.01); *C12M 27/00* (2013.01); *C12M 29/00* (2013.01); *C12M 41/40* (2013.01); *C12M 41/46* (2013.01); *B01L 2300/0816* (2013.01); *B01L 2400/0481* (2013.01); *B01L 2400/0655* (2013.01); *B01L 2400/082* (2013.01)

(58) Field of Classification Search
CPC ........ B01L 3/502746; B01L 3/502761; C12M 21/08; C12M 23/04; C12M 23/16; C12M 23/24; C12M 23/40; C12M 23/48; C12M 27/00; C12M 29/10
See application file for complete search history.

MULTI-ORGAN CHIP WITH IMPROVED LIFE TIME AND HOMOEOSTASIS

BACKGROUND ART

Miniaturized three dimensional (3D) organ or organoid culture systems are of increasing academic and economic interest. These 3D culture systems are aimed to allow investigation of how organs work and behave under certain stimuli as well as to test the effect of chemical compounds or compositions on particular organs or groups thereof and to study the pharmacokinetic behaviour of such compounds or compositions. In particular with regard to safety testing of chemical compounds, alternatives are required to replace animal experiments and to generate data which can more easily be used to efficiently and reliably predict safety in humans. The quality of such an in vitro 3D culture system will depend on its ability to reflect as closely as possible the physiological function and environment of the respective organ or organoid. This goal can only be achieved if the organs are not considered as separate, independent objects but if the complexity of interaction between different organs in an organism is mimicked as closely as possible. In order to allow for generation of meaningful data, it is required that the culture system remains stable for a prolonged period of time. However, most of the known 3D culture systems known today reflect only one cell type or model only one type of organ or organoid. 3D culture systems which take into account multiple organs and which allow dynamic culture of these multiple organs have only recently been described.

In WO2009/146911 A2 an organ-on-a-chip device has been presented. This organ-on-a-chip device is designed to be self-contained and sensor controlled. The device allows establishing or maintaining organs or organoids as well as stem cell niches in a miniaturized chip format. The organ-on-a-chip device can comprise a multiplicity of organ growth sections comprising an organ or organoid, a medium feed reservoir and a medium waste reservoir functionally connected to each other such that the organs or organoids of the organ growth section can be fed with medium from the medium feed reservoir and that degradation products and waste can be disposed via the medium waste reservoir. Although this model allows the simultaneous culture of more than one organ on one chip, this device does not allow for interaction and cross-talk between different organs on the chip. Furthermore, this device does not reflect all functions necessary to achieve homeostasis of the culture system over a prolonged period of time.

In WO 2012/016711 A1 a 3D cell culture model is presented comprising one or more organ growth sections, a self-contained circulation system configured to supply organs or organoids cultured in the organ growth sections with nutrients and a extra-capillary fluid or waste collector to collect interstitial fluid and degradation products from the organ growth sections. This system allows for simultaneous culture of more than one organ and mimics a vascular system supplying and interconnecting the different organs. Thus, this system allows for interaction and cross-talk between the organs or organoids of the system. However, this device does not reflect all functions necessary to achieve homeostasis of the culture system over a prolonged period of time.

SUMMARY OF THE INVENTION

The present invention relates to a multi-organ-chip device which mimics the basic functions of an organism necessary for organ and/or organism homeostasis. The multi-organ-chip device of the present invention is designed to reflect a self-contained circulation system mimicking the blood system of a higher organism which supplies a number of different organ equivalents. The organ equivalents are selected and arranged in such a way that the basic functions of food supply, waste removal and oxygen supply are represented and fully functional to maintain homeostasis of the organ equivalents over a prolonged period of time.

A multi-organ-chip device is provided, the device comprising
 a base layer;
 an organ layer arranged on the base layer;
 an antra layer arranged on the organ layer; and
 an actuator layer;
wherein
 the base layer is configured to provide a solid support for the further layers;
 the organ layer is configured to comprise
  a multiplicity of individual organ equivalents, each organ equivalent comprising one or more organ growth sections, each of the organ growth sections being configured to comprise an organoid cavity for housing at least one organoid of an organ and to comprise a micro-inlet and a micro-outlet for fluid communication between the organoid cavity of the organ growth section and a self-contained circulation system, wherein the organ layer comprises at least one organ equivalent configured to represent the organs lung, small intestine, spleen, pancreas, liver, kidney and bone marrow, respectively, and
  a self-contained circulation system configured to be in direct fluid communication with the organ growth sections of the organ layer via the micro inlets and outlets of the organ growth sections;
 the antra layer is configured to comprise a multiplicity of cavities and tubes arranged to be in fluid communication with selected organ equivalents or organ growth sections in order to allow for exchange of fluids between cavities and organ growth sections; and
 the actuator layer is configured to comprise a multiplicity of actuators arranged and configured to regulate a pressure force applied on a selected organ equivalent, the self-contained circulation system and/or part thereof.

Further details and preferred embodiments of the invention are defined in the specification below and in the claims.

DETAILED DESCRIPTION OF THE INVENTION

In the following the present invention is described in more detail. Unless specified otherwise, all technical and scientific terms used herein have the same meaning as commonly understood by a person skilled in the pertinent art. If a first layer or object is specified to be located on top of a second layer or object, the first layer or object may be located directly on top of the second layer or object or there may be present another layer or object in between the first and second layer or object.

The multi-organ-chip device of the invention is composed of a number of layers with different functionalities. The multi-organ-chip comprises a base layer, an organ layer, optionally an organ-holder layer, an antra layer and an actuator layer.

The base layer is configured to provide a solid support for the further layers such that the multi-organ-chip device can be easily handled and manipulated. Preferably said base layer is made of a transparent material. This has the advantage that the organ layer is optically accessible from the bottom side and, thus, allows observation of organoids in the organ growth section during culture by microscopy, e.g. by 2 Photon microscopy. Since the base layer is made of transparent material, the organ layer is accessible from the bottom side and allows for fluorescence ratio imaging for local interstitial pH measurement, phosphorescence quenching microscopy of interstitial $pO_2$ and infrared spectroscopy to detect physiological stress.

Preferred materials for the base layer comprise glass and optically transparent synthetic polymers like e.g. polystyrol (PS), polycarbonate (PC), polysiloxane and/or polydimethylsiloxane (PDMS).

In order to monitor the status of the device and to allow controlled culture of the organoids, the base layer may comprise one or more sensors configured and arranged to measure signals emitted from and/or to transmit signals to one or more of the organ equivalents, organ growth sections and/or the self-contained circulation system. Sensors are used which exhibit high sensitivity in order to allow for exact measurement even on small sample volumes. Preferably the base layer comprises sensors for the main parameters of human organismal homeostasis such as organoid or cell viability, temperature, pH, fluid balance, pressure, flow volume, oxygen pressure or oxygen consumption, nutrient consumption, fluid adsorption, intestinal juice secretion, albumin synthesis, bile synthesis, urea excretion, ion balance, osmolality and electrical coupling. Sensors which may be used include but are not limited to pH sensors, $pO_2$ sensors, analyte capture sensors, conductivity sensors, plasmon resonance sensors, temperature sensors, $CO_2$ sensors, NO sensors, chemotaxis sensors, cytokine sensors, ion sensors, pressure sensors, potentiometric sensors, amperometric sensors, flow-through sensors, fill sensors, impedance sensors, electromagnetic field sensors, surface acoustic wave sensors, and metabolic sensors. Preferably the base layer comprises at least the following set of sensors:

2 $pO_2$ sensors configured and located to measure $pO_2$ in the fluid of the self-contained circulation system of the organ layer, preferably one $pO_2$ sensor is located under the arteriolar transport channel in the vicinity of its origin from the lung equivalent and one $pO_2$ sensor is located under the venular transport channel in the vicinity of its origin from the lung equivalent;

4 trans epithelial/endothelial electrical resistance (TEER) sensors to identify leakage in the self-contained circulation system (if resistance between two of the TEER sensors is 0 leakage is likely), preferably two TEER sensors are located in the self-contained circulation system e.g. one TEER sensor is located in the vicinity of the origin of the arteriolar transport channel from the lung equivalent and one TEER sensor is located at end of the arteriolar transport channel most distant from the origin of the arteriolar transport channel from the lung equivalent, two TEER sensors are configured and located in the liver equivalent, optionally there may be two additional TEER sensors present configured and located in the skin or intestine equivalent all together to monitor the functionality of cellular barriers such as epithelial or endothelial barriers between the orgrans and the blood stream;

electrical sensors, which couple to biological neuronal ganglions, configured and located to be in contact with such ganglions in the organ equivalents.

The multi-organ-chip device of the invention comprises an organ layer located on top of the base layer. The organ layer is configured to comprise a multiplicity of individual organ equivalents, each organ equivalent comprising one or more organ growth sections. Each of the organ growth sections of the organ layer is configured to comprise an organoid cavity for housing one organoid of a specific organ type. Each organ growth section is configured to comprise a micro-inlet and a micro-outlet for fluid communication between the organoid cavity of the organ growth section and the self-contained circulation system of the organ layer. The organ layer comprises at least one organ equivalent configured to represent the organs: lung, small intestine, spleen, pancreas, liver, kidney and bone marrow, respectively. The organ layer may comprise additional organ equivalents like e.g. organ equivalents of skin, testes, brain and/or adipose tissue. Furthermore, the organ layer comprises a self-contained circulation system configured to be in direct fluid communication with the organ growth sections of the organ layer via the micro inlets and outlets of the organ growth sections of the organ equivalents.

As used herein, the term "organ equivalent" refers to all organ growth sections which comprise organoids or one particular organ type. All organs and systems of an organism, e.g. of a human organism, are built up by multiple, identical, functionally self-reliant, structural units, the organoid units. These organoid units are of very small dimensions, from several cell layers up to a few millimetres. Liver lobuli, nephrons of kidney, dermis and epidermis of skin, gut mucosa, Langerhans' islets of pancreas, grey and white matter of brain cortex and cerebellum and adult quiescence-promoting stem cell niches are a small selection of examples of such human organoid structures, all with a prominent functionality and highly variable conglomerate geometry. Due to distinguished functionality, a high degree of self-reliance and multiplicity of such micro-organoids within the respective organ, their reactivity pattern to any substances seems to be representative of the whole organ. Nature created very small but sophisticated biological structures to realize most prominent functions of organs and systems. Multiplication of these organoid structures within a given organ is nature's risk management tool to prevent total loss of functionality during partial organ damages. On the other hand, this concept has allowed the easy adjustment of organ size and shape to the needs of a given species—for example liver in mice and man—still using an established master plan to build up the single functional organoid unit. A unique and outstanding chance for substance testing predictive to human exposure lies in the establishment of equivalents of human micro-organoids in vitro. In the present invention, "organoids" means artificial, de novo generated, functional cell aggregates of different types of cells in vitro that show at least one organ or tissue function, preferably shows the majority of or essentially all organ or tissue functions. Thus, in the multi-organ-chip device of the present invention an organ equivalent is represented by one or more organ growth sections each organ growth section comprising an organoid cavity for housing one organoid of the respective organ type. Thus, the size of an organ equivalent can easily be adjusted by choosing the appropriate number of organ growth sections or organoids of the respective organ type.

The skilled person is well aware of the structure of an organoid of a given organ and knows how to produce said organoid. In the following some examples of organoids of specific organs are provided: alveolae form organoids of the lung, Langerhans' islets form organoids of the pancreas, white and red pulpae form organoids of the spleen, villi form organoids of the small intestine, lobule form organoids of the liver, nephrons form organoids of the kidney, units of bone marrow, bone and cartilage form organoids of the bone marrow, appendices form units of the skin, clusters form organoids of adipose tissue, follicle form organoids of the testes and cerebrellar cortex form organoids of the brain.

The liver organoid may be a liver lobulus of hexagonal shape with a volume of 1.2 to 2.2 mm$^3$.

The lung organoid may be a lung alveola of spheroid shape and with a surface of 0.15 to 0.25 mm$^2$.

The pancreas organoid may be a Langerhans' islet surrounded by exocrine tissue, all organized in spheroid shape and with a volume of 0.2 to 0.5 mm$^3$.

The spleen organoid may be white and red pulpa tissue of spheroid shape with a volume of 0.3 to 0.6 mm$^3$.

The small intestine organoid may be a villus of pillar shape with a surface of 0.2 to 0.4 mm$^2$.

The kidney organoid may be a kidney nephron with a spheroid capsula and a cylindrical tubulus and a filtration surface of 6 to 7.5 mm$^2$.

The bone marrow organoid may be a unit of macroporous shape formed of bone marrow, bone and cartilage with a volume of 0.006 to 0,008 mm$^3$.

The skin organoid may be a segment of hexagonal shape containing appendices, having a surface of 1.2 to 2 mm$^2$.

The adipose tissue organoid may be an adipose cluster of spheroid shape with a volume of 0.0004 to 0.0006 mm$^3$.

The testes organoid may be a testes follicle of spheroid shape with a volume of 0.006 to 0,008 mm$^3$.

The brain organoid may be a cerebral cortex column of cylindrical shape and a surface of 0.02 to 0.03 mm$^2$.

The organ layer may be designed such that:
- an organ growth section of the liver equivalent is configured to provide an organoid cavity for housing 5 to 15 liver organoids, wherein each liver organoid is a liver lobulus, preferably the organoid cavity is configured to house 10 liver organoids;
- an organ growth section of the lung equivalent is configured to provide an organoid cavity for housing 2000 to 4000 lung organoids, wherein each lung organoid is a lung alveola, preferably the organoid cavity is configured to house 3000 lung organoids;
- an organ growth section of the pancreas equivalent is configured to provide an organoid cavity for housing 5 to 15 pancreas organoids, wherein each pancreas organoid is a Langerhans' islet, preferably the organoid cavity is configured to house 10 pancreas organoids;
- an organ growth section of the spleen equivalent is configured to provide an organoid cavity for housing 5 to 15 spleen organoids, wherein each spleen organoid is a white and red pulpa, preferably the organoid cavity is configured to house 10 spleen organoids;
- an organ growth section of the small intestine equivalent is configured to provide an organoid cavity for housing 40 to 80 small intestine organoids, wherein each small intestine organoid is a villus, preferably the organoid cavity is configured to house 60 small intestine organoids;
- an organ growth section of the kidney equivalent is configured to provide an organoid cavity for housing 10 to 30 kidney organoids, wherein each kidney organoid is a nephron, preferably the organoid cavity is configured to house 20 kidney organoids; and
- an organ growth section of the bone marrow equivalent is configured to provide an organoid cavity for housing 1000 to 2000 bone marrow organoids, wherein each bone marrow organoid is a unit formed of bone marrow, bone and cartilage, preferably the organoid cavity is configured to house 1400 bone marrow organoids.

In addition, the organ layer may be designed such that:
- an organ growth section of the skin equivalent is configured to provide an organoid cavity for housing 10 to 20 skin organoids, wherein each skin organoid is a skin appendix, preferably the organoid cavity is configured to house 15 skin organoids;
- an organ growth section of the adipose tissue equivalent is configured to provide an organoid cavity for housing 200.000 to 300.000 adipose tissue organoids, wherein each adipose tissue organoid is an adipose cluster, preferably the organoid cavity is configured to house 240.000 adipose tissue organoids;
- an organ growth section of the testes equivalent is configured to provide an organoid cavity for housing 10 to 20 testes organoids, wherein each testes organoid is a testes follicle, preferably the organoid cavity is configured to house 15 testes organoids; and
- an organ growth section of the brain equivalent is configured to provide an organoid cavity for housing 100 to 300 brain organoids, wherein each brain organoid is a cerebral cortex column, preferably the organoid cavity is configured to house 200 brain organoids.

Each of the organ equivalents may be configured to house a number of organoids which is proportional to the number of organoids present in average in the respective organ of a mammalian organism, preferably of a human. In order to represent an organism, it is advantageous to select the size of all the organ equivalents of the multi-organ-chip device of the invention to reflect the relative proportionality in organ size under physiological condition in the organism. Preferably all organ equivalents of the multi-organ-chip device are reduced in size by the same predetermined proportionality factor. This proportionality factor may vary depending on the intended size of the multi-organ-chip device, a preferred proportionality factor is 0.00001 (1/100.000). If a human organism is to be represented, the multi-organ-chip device is preferably configured to comprise:

1 liver organoid,
300 lung organoids,
1 pancreas organoid,
1 spleen organoid,
6 small intestine organoids,
2 kidney organoids,
140 bone marrow organoids, and optionally
1 or 2 skin organoids,
24000 adipose organoids,
1 or 2 testes organoids,
20 brain organoids,
or a multiple thereof.

In a particular preferred embodiment, the multi-organ-chip device is preferably configured to comprise:

10 liver organoid,
3000 lung organoids,
10 pancreas organoid,
10 spleen organoid,
60 small intestine organoids,
20 kidney organoids,
1400 bone marrow organoids, and optionally
15 skin organoids,
240.000 adipose organoids,
15 testes organoids,
200 brain organoids,
or a multiple thereof.

Preferably, an organ growth section further comprises one or more stem cell niches. In order to provide a system which can be operated under homeostatic condition for a prolonged period of time, it is advantageous to provide a source of cells which can facilitate cell turn-over within an organoid. Each organ has a certain turn-over time during which the cells of the organ are replaced by new cells. This cellular turn-over of an organ ensures that the cells of an organ are vital and fully functional. Said turn-over can be mimicked by introducing a stem cell niche for one, some or all organ equivalents of the multi-organ-chip device. Said stem cell niches can be part of one, some or all organ growth sections of an organ equivalent.

The structure and way of manufacturing of such organ growth sections including organ cavities and stem cell niches have already been described in WO 2012/016711 A1 and WO 2009/146911 A2, the disclosure of which are incorporated herein by reference.

The organ layer may be made of a suitable material. Preferred materials comprise SiO2, glass, and synthetic polymers. Preferred synthetic polymers comprise polystyrol (PS), polycarbonate (PC), polyamide (PA), polyimide (PI), polyetheretherketone (PEEK), polyphenylenesulfide (PPSE), epoxide resin (EP), unsaturated polyester (UP)5 phenol resin (PF), polysiloxane, e.g. polydimethylsiloxane (PDMS), melamine resin (MF), cyanate ester (CA), polytetrafluoroethylene (PTFE) and mixtures thereof. Particularly preferred synthetic polymers are optically transparent and include, e.g. polystyrol (PS), polycarbonate (PC), and polysiloxane, e.g. polydimethylsiloxane (PDMS). A particularly preferred material comprises PDMS.

The organ layer comprises a self-contained circulation system. The self-contained circulation system is designed to mimic the vascular system of an organism and, thus, supplies all organ equivalents of the multi-organ-chip device of the invention with nutrients, $O_2$ and allows for interaction and cross-talk between the organ equivalents. The presence of said self-contained circulation system is vital for homeostasis of the whole multi-organ-chip device. The term "self-contained" refers to the fact that a fluid is circulatable in the circulation system and that preferably there is no fluidic connection for continuously providing fluid, e.g. medium, blood or a blood equivalent, from an external reservoir into the circulation system. In this context, "external" means that the reservoir is not an integral part of the circulation system or the multi-organ-chip device, e.g. is not connected via a tubing to the circulation system. If substances, e.g. nutrients and/or fluids, have to be replenished during the course of incubation it is preferred that such nutrients or fluids are supplied discontinuously through an injection port, which is preferably located in an arteriolar or venular transport channel of the circulation system or which is located in the antra layer.

The self-contained circulation system is configured to be in direct fluid communication with the organ growth sections of the organ equivalents of the organ layer via the micro inlets and outlets of said organ growth sections. The structure and way of manufacturing of such a self-contained circulation system has already been described in WO 2012/016711 A1, the disclosure of which is incorporated herein by reference. The inner surface of the self-contained circulation system can be lined with endothelial cells and optionally smooth muscle cells.

The self-contained circulation system comprises:
an arteriolar transport channel, which directly connects the micro-outlets of the organ growth sections of the lung equivalent with the micro-inlets of the organ growth sections of the organ layer in order to allow for transport of fluid with high $pO_2$ to said organ growth sections; and
a venular transport channel, which directly connects the micro-outlets of the organ growth sections with the micro inlets of the organ growth sections of the lung equivalent in order to allow for transport of fluid with low $pO_2$ from the organ growth sections to the lung equivalent.

The self-contained circulation system can be filled with a fluid capable of transporting nutrients and $O_2$ to the organ equivalents. Preferably said fluid is blood or a blood equivalent.

The fluid in the self-containing circulation system is circulated in a directed way by concerted action of actuators of the actuator layer of the multi-organ-chip device. By doing so, it is possible to mimic not only an adequate pressure within the circulation system which corresponds to the pressure in the vasculature of an organism but also allows mimicking heart beat. Thus, the self-contained circulation system of the multi-organ-chip device of the invention is suitable to provide shear forces and micro-environment that corresponds to the situation found under physiological conditions.

The self-contained circulation system may be configured such that the micro-outlets of the organ growth sections of small intestine, spleen and pancreas equivalents are connected to be in direct fluid communication with each other and with additional micro-inlets of the organ growth sections of the liver equivalent so as to allow for fluid communication between spleen, pancreas, small intestine and liver equivalent in such a way that fluid communication from spleen, pancreas and small intestine towards the venular transport channel of the self-contained circulation system can occur solely via passage through the liver equivalent. This architecture allows mimicking the basic functions of the digestive system of a higher organism like e.g. a human. The advantage of such architecture is that the multi-organ-chip device can be cultured over a prolonged time by supplying the small intestine equivalent with nutrients from a reservoir located in the antra layer. The organ equivalents of the multi-organ-chip device of the invention will then be supplied with nutrients which have passed a digestive system. Thus, nutrients are provided in a form and manner which is more comparable to the physiological condition in an organism. There is no longer any need for an external medium reservoir which is constantly fed in the circulation system to supply the organ equivalents.

The self-contained circulation system and the organ equivalents are preferably configured such that the arteriolar transport channel originating from the lung equivalent exhibits in flow direction bifurcations at which arteriolar channels are branching off supplying the organ equivalents. The fluid passing through a given organ equivalent is channeled back into the venular transport channel via venular channels branching off from the venular transport channel at respective bifurcations. Preferably, the self-contained circulation system and the organ equivalents are configured such that the arteriolar transport channel originating from the lung equivalent exhibits in flow direction:
a first bifurcation at which a first arteriolar channel is branching off supplying the small intestine, the spleen and the pancreas equivalent;
a second bifurcation at which a second arteriolar channel is branching off supplying the liver equivalent;
a third bifurcation at which a third arteriolar channel is branching off supplying the kidney equivalent;

a fourth bifurcation at which a fourth arteriolar channel is branching off supplying the kidney equivalent;

a fifth bifurcation at which a fifth arteriolar channel is branching off supplying the bone marrow;

an optional sixth bifurcation at which a sixth arteriolar channel is branching off supplying a skin equivalent;

an optional seventh bifurcation at which a seventh arteriolar channel is branching off supplying an adipose tissue equivalent;

an optional eighth bifurcation at which an eighth arteriolar channel is branching off supplying a testes equivalent; and an optional ninth bifurcation at which a ninth arteriolar channel is branching off supplying a brain equivalent.

The self-contained circulation system is configured such that the diameter of the arteriolar transport channel in flow direction is constantly reduced such that the sum of cross-sectional areas of all arteriolar transport channels including all bifurcations at a given distance from the lung equivalent remains constant and wherein in the venular transport channel said reduction in diameter is constantly reverted in flow direction such that the sum of cross-sectional areas of all venular transport channels including all bifurcations at a given distance from the lung equivalent remains constant.

The organ layer may be configured such that the organoid cavities of the organ growth sections are open on the side opposed to the basal layer. This allows applying the organoids or precursor cells to the respective organoid cavities before the multi-organ-chip device is fully assembled. In this case, the multi-organ-chip device further comprises an otherwise optional organ-holder layer. The organ-holder layer is arranged between the organ layer and the antra layer. The organ-holder layer is configured to seal and/or stabilize the organ layer in such a way that for selected organ equivalents communication with the antra layer is maintained. The organ-holder layer may be provided as a layer of 50 to 500 µm thickness, preferably of a thickness of 100 to 300 µm, more preferably of a thickness of 200 µm. The organ-holder layer may be made of a material which comprises or consists of a synthetic polymer like e.g. polystyrol (PS), polycarbonate (PC), polysiloxane and/or polydimethylsiloxane (PDMS). Preferably the material comprises or consists of polycarbonate. Specifically in areas, where the organ-holder layer covers an organ equivalent which has excretory function and/or produces considerable amount of interstitial fluid, like kidney, liver, spleen and small intestine, the organ-holder layer is configured to allow fluid communication between the organ layer and the antra layer. This fluid communication can be achieved e.g. by providing pores within the organ-holder layer, preferably by providing pores with an average diameter of 5 to 7 µm. Alternatively or in addition the thickness of the organ-holder layer in an area allowing fluid communication between the organ layer and the organ-holder layer can be reduced to an average thickness of 5 to 15 µm, preferably to 10 µm.

The multi-organ-chip device of the invention comprises an antra layer arranged on top of the organ layer. The antra layer is configured to comprise a multiplicity of cavities and tubes arranged to be in fluid communication with selected organ equivalents or organ growth sections in order to allow for exchange of fluids between cavities of the antra layer and organ growth sections of the organ layer. A number of organs have excretory functions and/or produce considerable amounts of interstitial fluid which have to be dissipated if culture or incubation over a prolonged period of time is envisaged. Especially since the fluid of the self-contained circulation system is circulated constantly without exchange and replacement, it is vital to dissipate degradation products from the system. In particular urine built in the kidney equivalent and faeces provided from the small intestine equivalent have to be eliminated from the system in order to allow operation of the multi-organ-chip device for a prolonged period of time under homeostatic conditions. Furthermore, since medium is not constantly fed into the system, a reservoir for supplying the small intestine equivalent with nutrients is required. Preferably this nutrient reservoir is not arranged within the organ layer itself but within the antra layer. This allows refilling the nutrient reservoir discontinuously during operation of the multi-organ-chip device without directly interacting with the organ layer.

The antra layer may be configured to comprise:

a cavity which is located on top of the small intestine equivalent and is in fluid communication with the small intestine equivalent and a nutrition reservoir such that the small intestine equivalent can be supplied with nutrients from the nutrition reservoir;

a cavity which is located on top of the small intestine and is in fluid communication with the small intestine equivalent and a faeces reservoir such that material excreted from the small intestine equivalent can be transported to the faeces reservoir;

a cavity which is located on top of the liver equivalent and is in fluid communication with the liver equivalent and the cavity which is located on top of the small intestine equivalent such that material excreted from the liver equivalent can be transported to the cavity which is located on top of the small intestine; and a cavity which is located on top of the kidney equivalent and is in fluid communication with the kidney equivalent and a urine reservoir such that the urine reservoir receives material excreted from the kidney equivalent.

The nutrition reservoir, the faeces reservoir, and the urine reservoir are integral part of the antra layer.

The antra layer may further comprise a port that allows introduction of chemical compounds, like e.g. test compounds, to the fluid of the self-contained circulation system and to take samples from the fluid of the self-contained circulation system.

The multi-organ-chip device of the invention comprises an actuator layer. The actuator layer is configured to comprise a multiplicity of actuators arranged and configured to regulate a pressure force applied on a selected organ equivalent, the self-contained circulation system and/or part thereof. In order to operate an organism under homeostatic conditions it is necessary to ensure controlled movement and application of force within the system. Obviously, blood in the vasculature has to be moved in order to ensure proper function. However, also intestinal peristaltic movement is necessary as well as compression and decompression of the lung in order to allow for air flow. In the multi-organ-chip device of the present invention said movement or introduction of force is facilitated via the actuators of the actuator layer. The configuration and arrangement of actuator elements in the actuator layer depends on the overall architecture of the multi-organ-chip device, in particular of the arrangement of organ equivalents within the organ layer. The actuators may be realized as air pressure-based actors that are configured to apply pressure force on an organ equivalent or the self-contained circulation system or a part thereof. These actuators may be controlled by an external device which may be programmable.

Preferably, the actuator layer comprises:
one or more actuators acting on the self-contained circulation system to allow for directed fluid movement in order to mimic heart beat;
one or more actuators acting on the antra layer to allow for directed movement in order to mimic intestinal peristaltic movement;
one or more actuators acting on the lung equivalent to allow for air-flow in order to mimic breathing;
one or more actuators acting on the bone marrow equivalent to allow for regulated compression in order to mimic bone compression;
one or more actuators acting on the arteriolar transport channel of the self-contained circulation system in order to mimic arteriolar constriction;
one or more actuators acting on the liver equivalent to allow for directed fluid movement in order to dissipate bile from the liver equivalent; and
one or more actuators acting on the antra layer to allow for directed fluid movement in order to dissipate urine from the kidney equivalent.

In a preferred embodiment of the multi-organ-chip device of the invention, the organ layer comprises or consists of polydimethylsiloxane (PDMS), the organ holder comprises or consists of polycarbonate, the antra layer comprises or consists of PDMS and/or the actuator layer comprises or consists of polycarbonate.

The present invention is directed to the multi-organ-chip device defined above and in the claims without organoids, cells and fluid. The present invention is also directed to the multi-organ-chip device defined above, wherein the multi-organ-chip device comprises the respective organoids, cells and fluids.

The multi-organ-chip of the present invention is characterized by its potential in prolonged operation in homeostatic condition and its closeness to a physiological organism. The multi-organ-chip can be applied in different settings depending on the content and architecture of the organ equivalents present on the device. In addition to applications in systemic safety testing, immunological, infectious and/or oncological models, the following preferred uses of the multi-organ-chip device of the invention are presented:

TABLE 1

Preferred uses of the multi-organ-chip device of the invention

| Organ systems | Use of the multi-organ-chip device for modelling of (not limited) |
|---|---|
| Circulatory: | blood vessel system capable of replicating the structural and hemodynamic microenvironment of in vivo vasculature; hematopoiesis, bone marrow |
| | Lymphatic system that represents aspects of circulatory and immune systems |
| | Models of arrhythmia, inotropy, chronotropy and distinct properties of cardiomyocytes in the AV and SV nodes. |
| | Integrated systems that include coronary vasculature and oxygen gradients across cardiac tissue |
| | Microsystems that can model disease pathologies such as long QT syndrome, cardiomyopathy |
| Endocrine: | Mimicking hypothalamic-pituitary-endocrine organ axes (e.g. adrenal, thyroid, parathyroid, gonadal, adipocytes) |
| | Pancreatic islets and/or its components (beta cells, alpha cells) |
| | Diseases involving dysregulated hormone release or endocrinopathies |
| | Individual and interconnected pathogenesis, treatment and complications of type 1 and type 2 diabetes |
| Gastrointestinal: | Salivary gland |
| | Gut including interaction with the microbiota |
| | Diseases of liver steatosis, liver toxicity, inflammatory bowel disease, esophageal and gut dysmotility, pancreatitis |
| Immune: | Innate and adaptive immune system, infant and adult immune system, gender-specific immune response, spleen |
| | Disease pathologies such as inflammation, complement activation, dendritic cell activation, autoimmunity, allergy, hypersensitivity, infectious disease |
| Integumentary: | Skin and related squamous mucosal epithelia that mimic the functions of a barrier, an immune organ (e.g., allergic reaction), a thermostatic regulatory organ, a sensory organ (e.g., touch, temperature, pain, itch) and a secretory organ (e.g., sebum, antimicrobial peptides), cornified and non-cornified oral mucosa |
| | Tissues that contain epidermal and dermal tissues with integrated melanocytes, immune cells, nerve endings and other relevant cell types |
| | Tissues that contain vasculature, hair follicles, sweat glands and other relevant sub-organ structures |
| | Testing of skin wound healing, irritation, allergic reaction, vaccine/adjuvant efficacy |
| | Skin disease models (e.g., psoriasis, fibrosis) |
| Musculoskeletal: | joint, bone homeostasis, spine, muscle and neuromuscular, tooth development and regeneration |
| | intra-membranous bone, vascularised bone, muscle (depicting dynamic workload, muscle types (cardiac vs skeletal), neuromuscular innervations), endochondrial bone, cartilage and connective tissues such as tendon and ligament |
| | Diseases of muscular dystrophies or diseases, neuromuscular disorders, osteoarthritis, rheumatoid arthritis, osteoporosis |

TABLE 1-continued

Preferred uses of the multi-organ-chip device of the invention

| Organ systems | Use of the multi-organ-chip device for modelling of (not limited) |
|---|---|
| Nervous: | Neuron-glia microenvironment, synaptic connections, blood-brain barrier or neurovascular unit, cortical architecture, eye and ocular tissues<br>Enabling assessment of aberrant circuit activation for seizure modelling, evaluation of hypoxic effects on inflammation in brain tissue<br>Diseases of neurodegeneration, neurodevelopmental disorders, seizures, learning and memory, addiction |
| Reproductive: | Vaginal-ectocervical equivalent, placenta (permeability, transport and metabolism of drugs); spermatogenesis; steroidogenesis; breast tissue/mammary gland and complex hormonal regulation<br>Diseases of infertility |
| Respiratory: | Mimicking airway reactivity, gas exchange in a non-leaky system, lung microsystem with tracheal, bronchial and mucociliary phenotype<br>Diseases of pulmonary hypertension, cystic fibrosis, bronchiospasm, asthma<br>Enabling evaluation of exposures to respiratory pathogens, smoke inhalation or inhalation of toxic substances |

In the following the invention is explained in more detail by way of an example.

FIGURES

Figure 7:
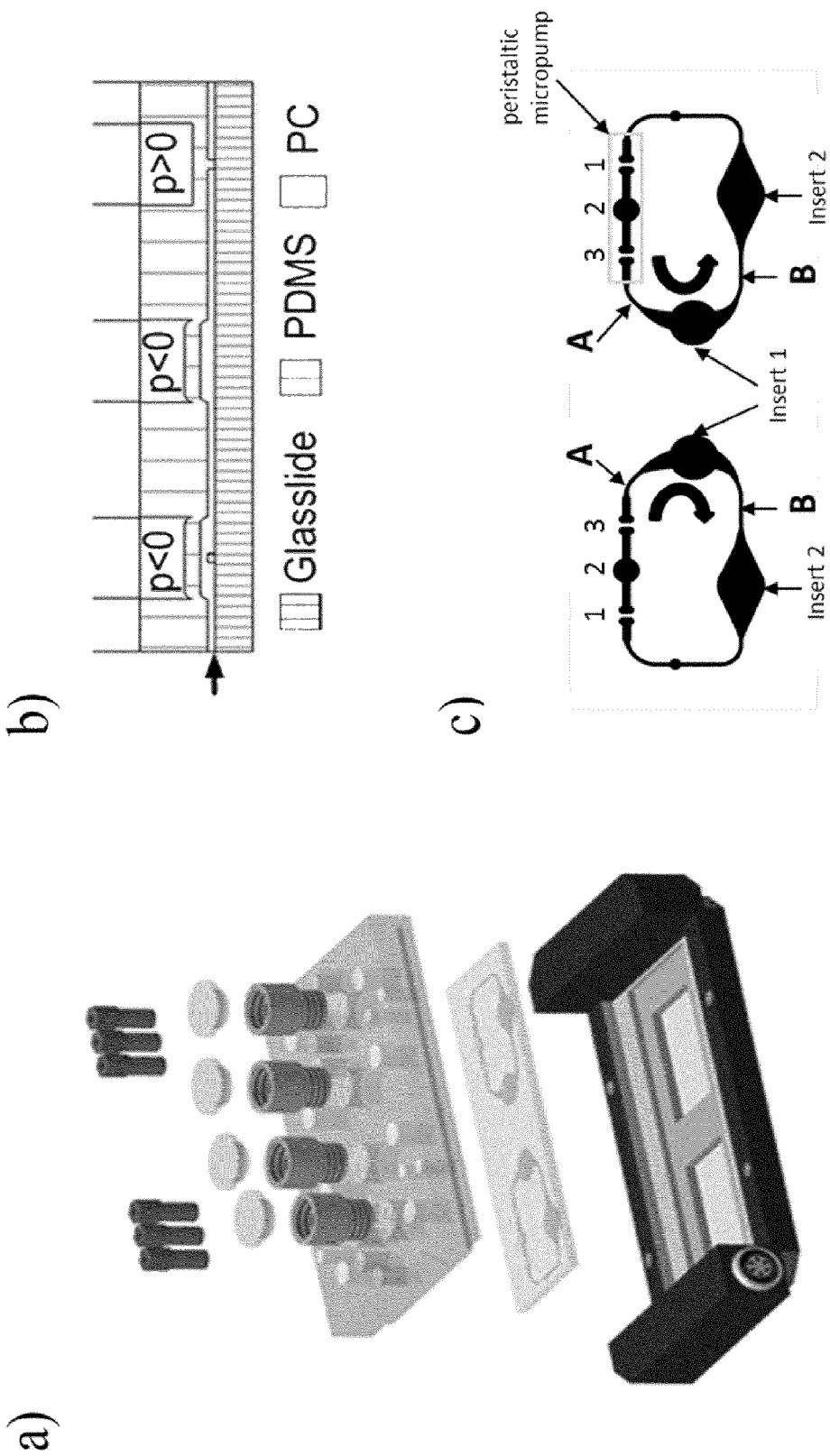

FIG. 7 shows a microfluidic multi-organ-chip (MOC) device at a glance. (a) Exploded view of the device comprising a polycarbonate CP, the PDMS-glass chip accommodating two microvascular circuits (footprint: 76 mm×25 mm; height: 3 mm) and a heatable MOC-holder. (b) Cross-section of a peristaltic on-chip micropump operated by programmed periodic compression and decompression of three successively arranged PDMS membranes (thickness: 500 μm); arrow indicates the direction of flow. (c) Top view of the MOC layout illustrating the two separate microfluidic circuits (channel height: 100 μm; width: 500 μm) each accommodating two insert areas (compartments) (insert diameter: 5 mm). Spots A and B of each circuit designate the position of non-invasive fluid flow and cell analysis.

Figure 8:
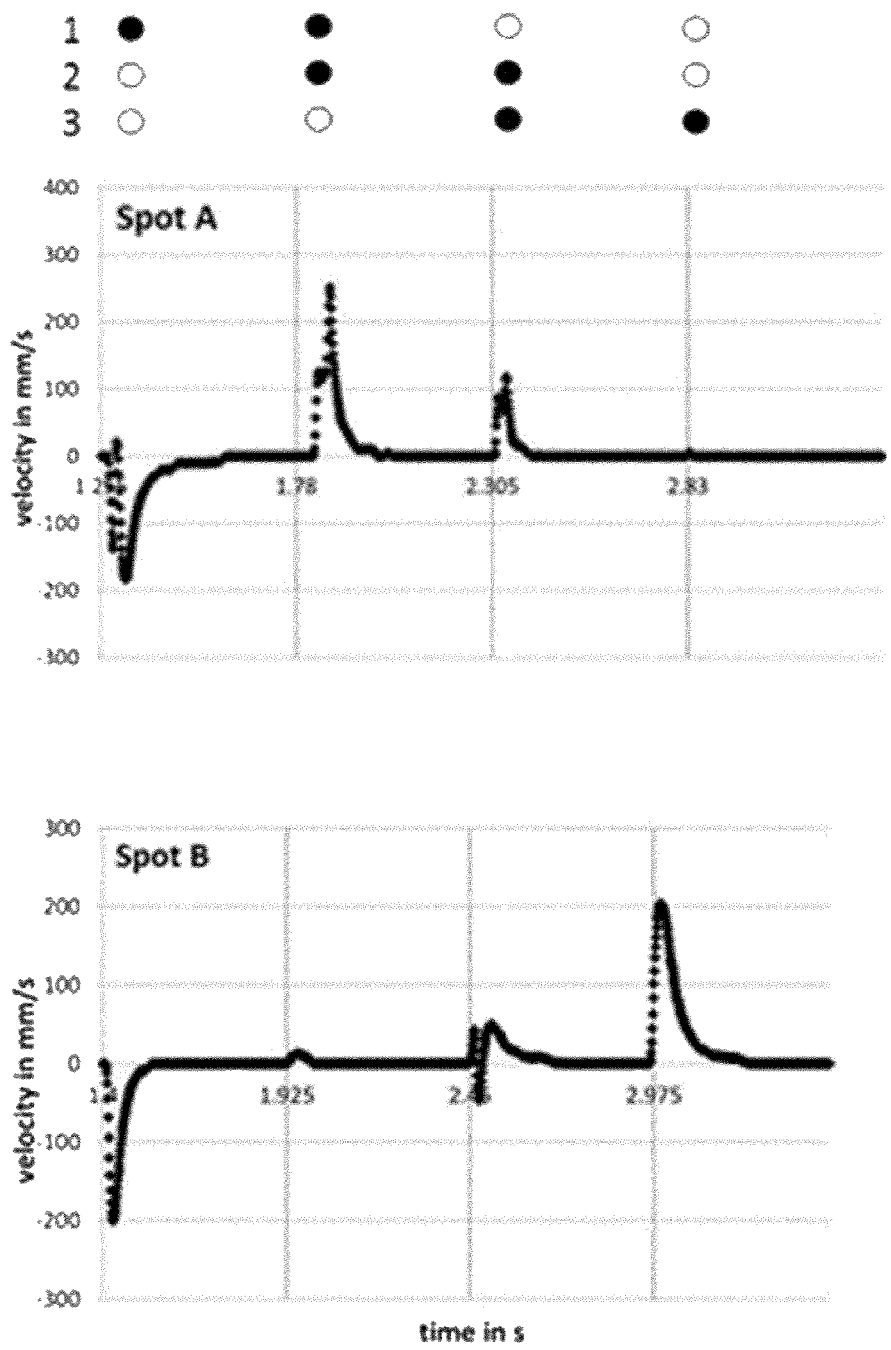
Figure 8:
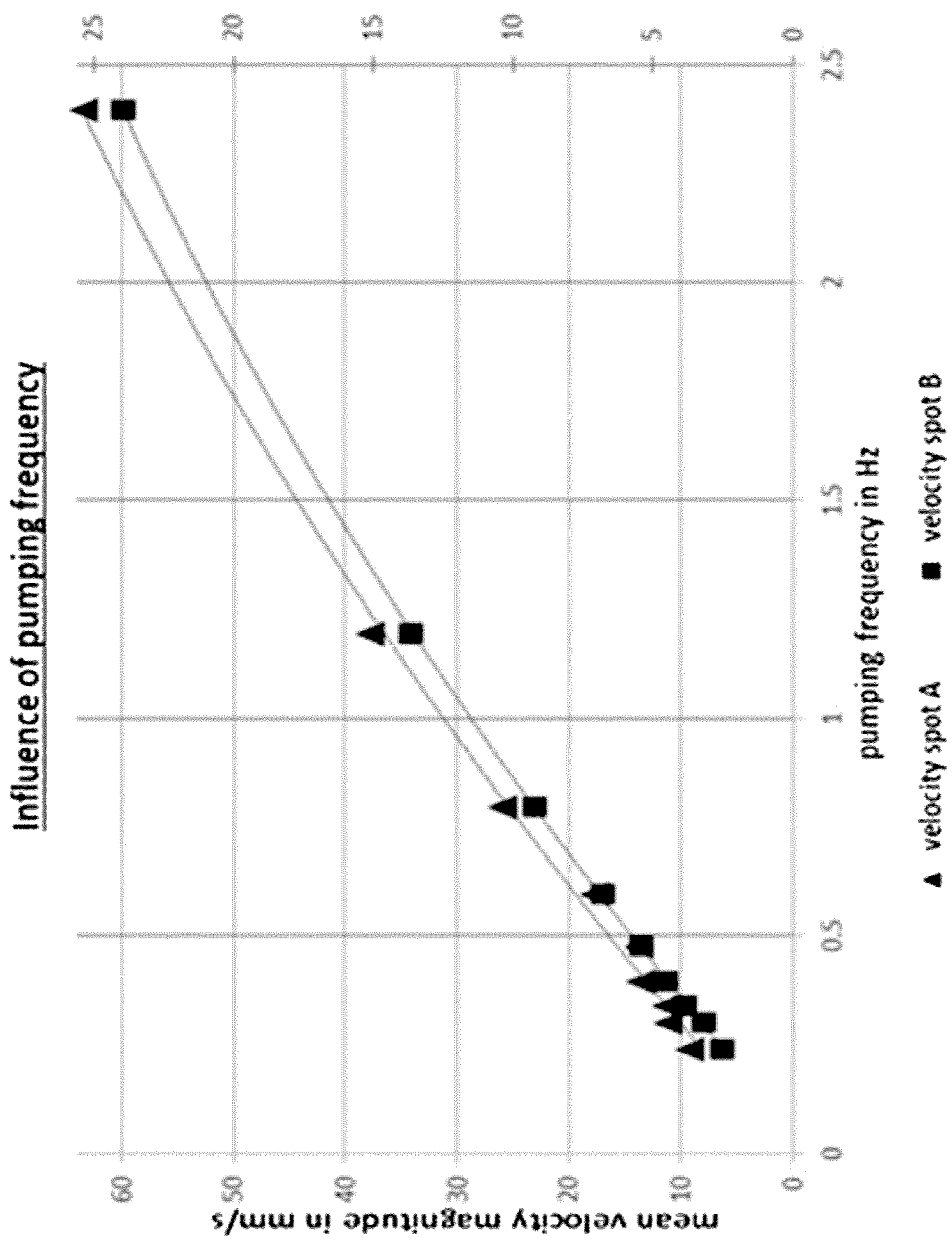

FIG. 8 shows evaluation of fluid dynamics in the MOC of FIG. 7. (a) Exemplary velocity profiles throughout the four stages of a full pumping cycle (frequency: 0.476 Hz) measured at the two discrete fluid flow analysis spots to underpin the pulsatile character of the fluid flow (black circle=open valve, white circle=closed valve). (b) Mean velocity magnitude (mm/s) and corresponding shear stress (dyn/cm$^2$) plotted against pumping frequencies (Hz) at both spots.

EXAMPLE

Example 1

Multi-Organ-Chip Device of the Invention

Figure 1:
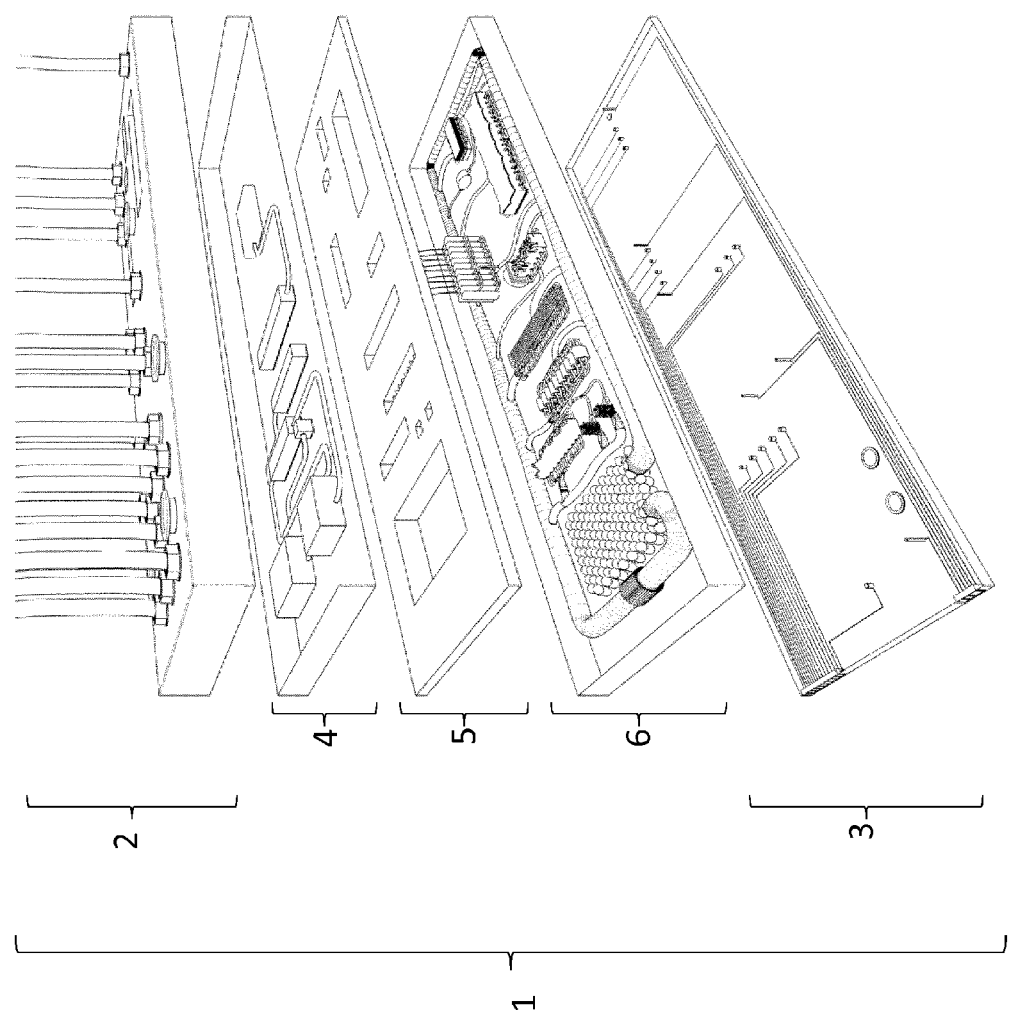
FIG. 1 shows a schematic overview of an embodiment of the multi-organ-chip device of the invention with all its layer structure.

As depicted in FIG. 1, the multi-organ-chip device 1 comprises a base layer 3, an organ layer 6, an organ holder layer 5, an antra layer 4 and an actuator layer 2.

Figure 6:
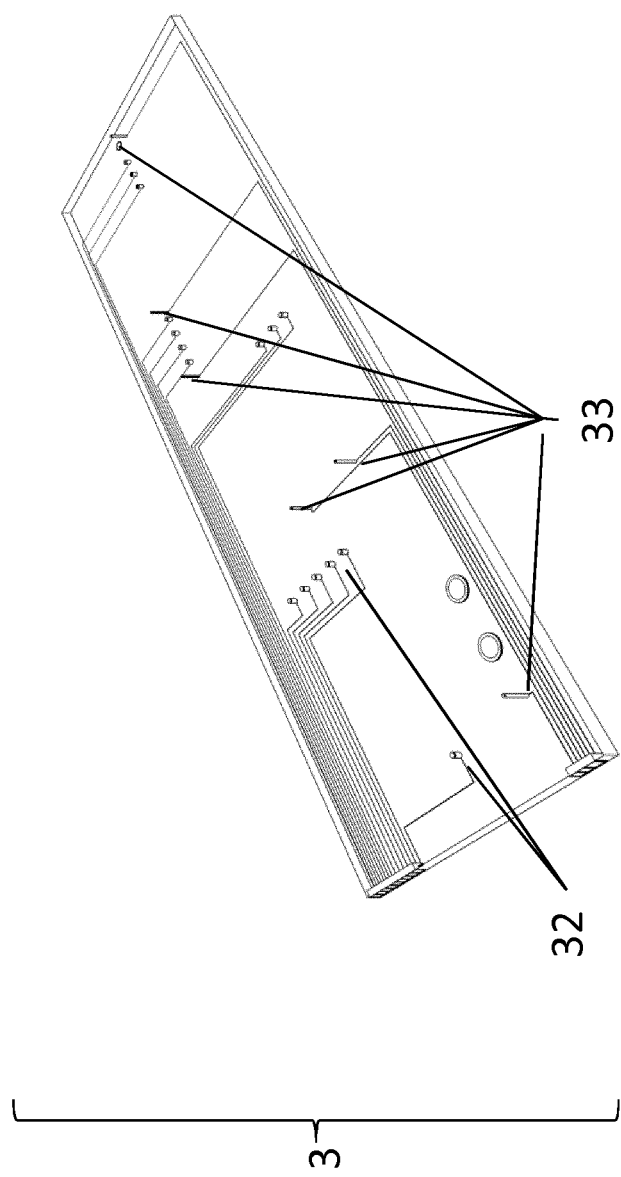
FIG. 6 shows a schematic top-down view on the base layer of the embodiment of FIG. 1.

As shown in FIG. 6, the base layer 3 is configured to provide a solid support for the further layers. The base layer 3 is made of glass or a transparent synthetic polymer like e.g. polystyrol (PS), polycarbonate (PC), polysiloxane and/or polydimethylsiloxane (PDMS). The base layer 3 also comprises a number of sensors 32 and 33 which are designed and arranged to monitor and control the system. Some of these sensors 32 are configured to apply electric stimuli to organ equivalents of the organ layer, other sensors 33 are configured to measure parameters of the system in order to ensure proper function. The base layer 3 comprises ports from which data acquired by the sensors can be extracted and used for other purposes like e.g. regulating the system.

Figure 5:
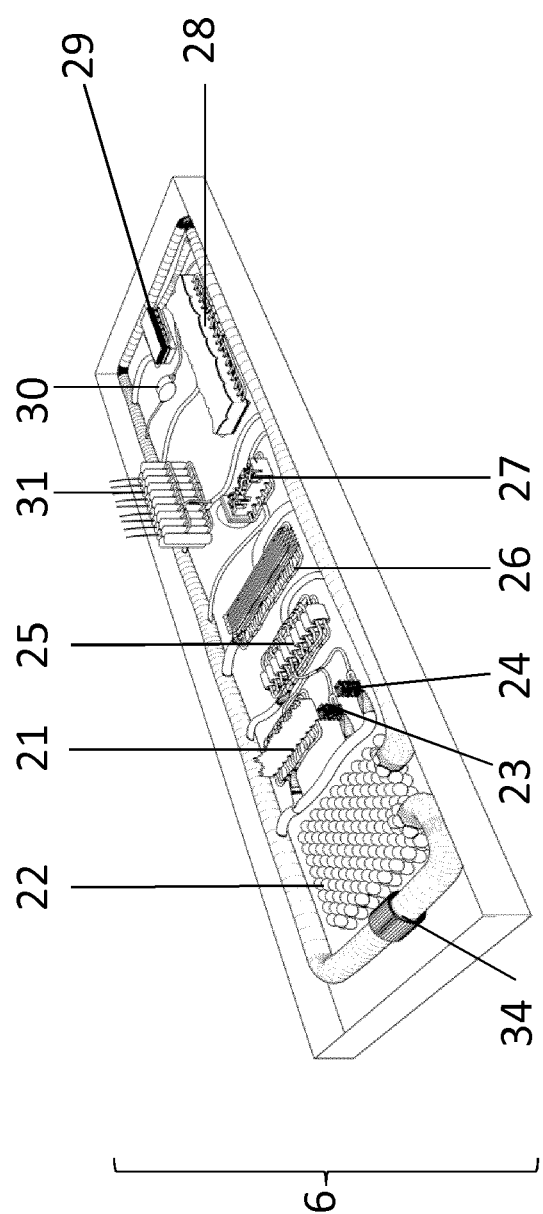
FIG. 5 shows a schematic top-down view on the organ layer of the embodiment of FIG. 1.

The organ layer 6 is shown in FIG. 5. The organ layer 6 is located on top of the base layer 3, is made of PDMS and is configured to comprise a multiplicity of individual organ equivalents, each organ equivalent comprising one or more organ growth sections, each of the organ growth section being configured to comprise an organoid cavity for housing at least one organoid of a given organ. The organ layer 6 comprises a lung equivalent 22, a small intestine equivalent 21, a spleen equivalent 23, a pancreas equivalent 24, a liver equivalent 25, a kidney equivalent 26, a bone marrow equivalent 27, an adipose tissue equivalent 28, a brain equivalent 29, a testes equivalent 30 and a skin equivalent 31. Each organ growth section comprises a micro-inlet and a micro-outlet for fluid communication between the organoid cavity of the organ growth section and a self-contained circulation system 34. The self-contained circulation system 34 is configured to be in direct fluid communication with the organ growth sections of the organ layer 6 via the micro inlets and outlets of the organ growth sections. The self-contained circulation system 34 comprises an arteriolar transport channel directly connecting the micro-outlets of the organ growth sections of the lung equivalent 22 with the micro-inlets of all other organ growth sections of the organ layer 6 in order to allow for transport of fluid with high pO₂ to said organ growth sections; and a venular transport channel directly connecting the micro-outlets of the organ growth sections with the micro inlets of the organ growth sections of the lung equivalent 22 in order to allow for transport of fluid with low pO₂ from the organ growth sections to the lung equivalent 22. The self-contained circulation system 34 is configured such that the micro-outlets of the organ growth sections of small intestine, spleen and pancreas equivalents 21, 23, 24 are connected to be in direct fluid communication with each other and with additional micro-inlets of the organ growth sections of the liver equivalent 25 so as to allow for fluid communication between spleen, pancreas, small intestine and liver equivalent 23, 24, 21, 25 in such a way that fluid communication from spleen, pancreas and small intestine equivalent 23, 24, 21 towards the venular transport channel of the self-contained circulation system 34 can occur solely via passage through the liver equivalent 25. The organ equivalents and the self-contained circulation system 34 are configured such that the arteriolar transport channel originating from the lung equivalent 22 exhibits in flow direction:

a first bifurcation at which a first arteriolar channel is branching off supplying the small intestine, the spleen and the pancreas equivalent 21, 23, and 24;

a second bifurcation at which a second arteriolar channel is branching off supplying the liver equivalent 25;

a third bifurcation at which a third arteriolar channel is branching off supplying the kidney equivalent 26;

a fourth bifurcation at which a fourth arteriolar channel is branching off supplying the bone marrow equivalent 27;

an optional fifth bifurcation at which a fifth arteriolar channel is branching off supplying the skin equivalent 31;

a sixth bifurcation at which a sixth arteriolar channel is branching off supplying the adipose tissue equivalent 28;

a seventh bifurcation at which a seventh arteriolar channel is branching off supplying the testes equivalent 30; and an eighth bifurcation at which an eighth arteriolar channel is branching off supplying the brain equivalent 29.

The diameter of the arteriolar transport channel in flow direction (from the lung equivalent 22 towards the other organ equivalents) is constantly reduced such that the sum of cross-sectional areas of all arteriolar transport channels including all bifurcations at a given distance from the lung equivalent 22 remains constant, and wherein in the venular transport channel said reduction in diameter is constantly reverted in flow direction (from the other organ equivalents towards the lung equivalent 22) such that the sum of cross-sectional areas of all venular transport channels including all bifurcations at a given distance from the lung equivalent remains constant.

The organ equivalents each are configured to house a number of organoids which is proportional to the number of organoids present in average in the respective organ of a mammalian organism, preferably of a human, wherein all organ equivalents of the multi-organ-chip device are reduced in size by the same predetermined proportionality factor, e.g. by a factor of 0.00001 (1/100,000).

The organ layer 6 is designed such that:

the organ growth section of the liver equivalent 25 is configured to provide an organoid cavity for housing 5 to 15 liver organoids, wherein each liver organoid is a liver lobulus, preferably the organoid cavity is configured to house 10 liver organoids;

the organ growth section of the lung equivalent 22 is configured to provide an organoid cavity for housing 2000 to 4000 lung organoids, wherein each lung organoid is a lung alveola, preferably the organoid cavity is configured to house 3000 lung organoids;

the organ growth section of the pancreas equivalent 24 is configured to provide an organoid cavity for housing 5 to 15 pancreas organoids, wherein each pancreas organoid is a Langerhans' islet, preferably the organoid cavity is configured to house 10 pancreas organoids;

the organ growth section of the spleen equivalent 23 is configured to provide an organoid cavity for housing 5 to 15 spleen organoids, wherein each spleen organoid is a white and red pulpa, preferably the organoid cavity is configured to house 10 spleen organoids;

the organ growth section of the small intestine equivalent 21 is configured to provide an organoid cavity for housing 40 to 80 small intestine organoids, wherein each small intestine organoid is a villus, preferably the organoid cavity is configured to house 60 small intestine organoids;

the organ growth section of the kidney equivalent 26 is configured to provide an organoid cavity for housing 10 to 30 kidney organoids, wherein each kidney organoid is a nephron, preferably the organoid cavity is configured to house 20 kidney organoids;

the organ growth section of the bone marrow equivalent 27 is configured to provide an organoid cavity for housing 1000 to 2000 bone marrow organoids, wherein each bone marrow organoid is a unit formed of bone marrow, bone and cartilage, preferably the organoid cavity is configured to house 1400 bone marrow organoids;

the organ growth section of the skin equivalent 31 is configured to provide an organoid cavity for housing 10 to 15 skin organoids, wherein each skin organoid is a skin appendix, preferably the organoid cavity is configured to house 15 skin organoids;

the organ growth section of the adipose tissue equivalent 28 is configured to provide an organoid cavity for housing 200.000 to 300.000 adipose tissue organoids, wherein each adipose tissue organoid is an adipose cluster, preferably the organoid cavity is configured to house 240.000 adipose tissue organoids;

the organ growth section of the testes equivalent 30 is configured to provide an organoid cavity for housing 10 to 20 testes organoids, wherein each testes organoid is a testes follicle, preferably the organoid cavity is configured to house 15 testes organoids; and the organ growth section of the brain equivalent 29 is configured to provide an organoid cavity for housing 150 to 250 brain organoids, wherein each brain organoid is a cerebral cortex column, preferably the organoid cavity is configured to house 200 brain organoids.

In the following Table 2 parameters are given for an organ layer 6 made of a PDMS layer with a height of 3 mm.

TABLE 2

| Organoid | length × width × height (mm) | Volume (mm3) | Reduction in cross-sectional area of circulation system at bifurcation (%) | Cross-sectional area of channel (mm2) | Cross-sectional area of branch (mm2) |
|---|---|---|---|---|---|
| alveola (lung) | 15 × 9 × 2 | 270 | 100 | 3.14 | |
| Langerhans' islets (pancreas) | 1 × 1 × 1 | 1 | 17.61 | 2.59 | 0.55 |
| white and red pulpa (spleen) | 1 × 1 × 1 | 1 | | | |
| villus (intestine) | 9 × 2 × 1.5 | 27 | | | |
| lobulus (liver) | 10 × 1.5 × 1.5 | 22.5 | 9.47 | 2.29 | 0.30 |
| nephron (kidney) | 12 × 2 × 2 | 48 | 18.13 | 1.72 | 0.57 |
| unit (bone-marrow) (bone marow: 5 mm + bone + cartilage: 1.5 mm = 6.5 mm) | 6.5 × 2 × 1.5 | 19.5 | 4.06 | 1.59 | 0.13 |
| appendices (skin) | 2 × 9 × 4 | 72 | 5.79 | 1.41 | 0.18 |
| cluster (adipose tissue) | 4 × 17 × 1.5 | 102 | 5.53 | 1.24 | 0.17 |
| follicle (testes) | 1 × 1 × 1.5 | 1.5 | 1.87 | 1.18 | 0.06 |
| cerebellar cortex (brain) | 5 × 2 × 1.5 | 15 | 11.46 | 0.82 | 0.36 |
| circulation system at shunt: | | | 24.91 | 0.78 | |

Figure 4:
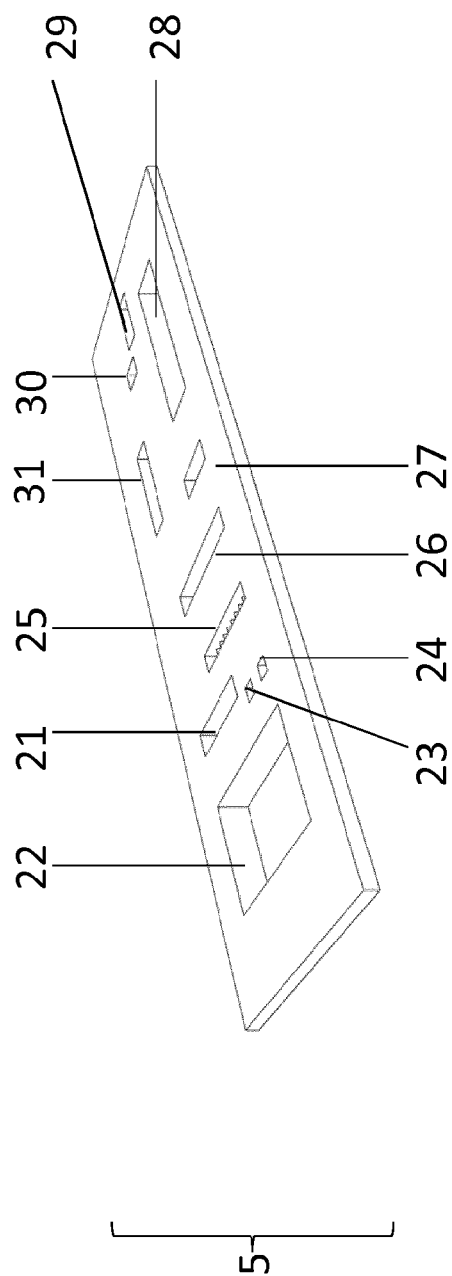
FIG. 4 shows a schematic top-down view on the organ-holder layer of the embodiment of FIG. 1.

The organ-holder layer 5 is arranged between the organ layer 6 and the antra layer 4, see FIG. 4. The organ-holder layer 5 is configured to seal and/or stabilize the organ layer 6 in such a way that for selected organ equivalents fluid communication with the antra layer 4 is maintained. The organ-holder layer 5 is provided as a layer with a thickness of 200 μm. The organ-holder layer 5 is made of a material which comprises or consists of polycarbonate (PC). In areas, where the organ-holder layer 5 covers one of the organ equivalents 21, 22, 23, 24, 25, 26, 27, 28, 29, 30, 31, the organ-holder layer 5 is configured to allow fluid communication between the organ layer 6 and the antra layer 4. In particular in areas where the organ-holder layer 5 covers an organ equivalent which has excretory function and/or produces considerable amount of interstitial fluid, like kidney 26, liver 25, spleen 23 and small intestine 21, this fluid communication can be achieved e.g. by providing pores within the organ-holder layer 5, preferably by providing pores with an average diameter of 5 to 7 μm. Alternatively or in addition, in an area allowing fluid communication between the organ layer 6 and the antra layer 4, the thickness of the organ-holder layer 5 can be reduced to an average thickness of 5 to 15 μm, preferably to 10 μm.

Figure 3:
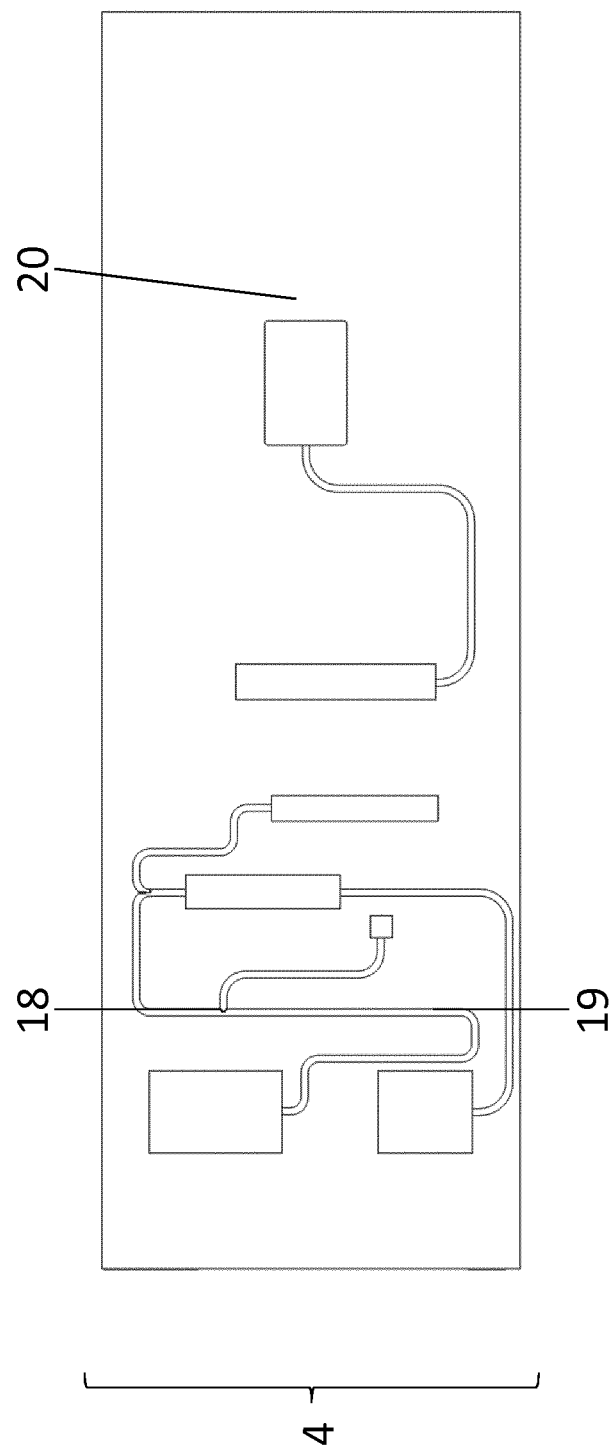
FIG. 3 shows a schematic top-down view on the antra layer of the embodiment of FIG. 1.

The antra layer 4 is depicted in FIG. 3 and is configured to comprise a multiplicity of cavities and tubes arranged to be in fluid communication with selected organ equivalents or organ growth sections of the organ layer 6 in order to allow for exchange of fluids between cavities and organ growth sections. The antra layer 4 comprises or consists of PDMS. The antra layer 4 is configured to comprise:
- a cavity which is located on top of the small intestine equivalent 21 and is in fluid communication with the small intestine equivalent 21 and a nutrition reservoir 18 such that the small intestine equivalent 21 can be supplied with nutrients from the nutrition reservoir 18;
- a cavity which is located on top of the small intestine equivalent 21 and is in fluid communication with the small intestine equivalent 21 and a faeces reservoir 19 such that material excreted from the small intestine equivalent 21 can be transported to the faeces reservoir 19;
- a cavity which is located on top of the liver equivalent 25 and is in fluid communication with the liver equivalent 25 and the cavity which is located on top of the small intestine equivalent 21 such that material excreted from the liver equivalent 25 can be transported to the cavity which is located on top of the small intestine equivalent 21; and
- a cavity which is located on top of the kidney equivalent 26 and is in fluid communication with the kidney equivalent 26 and a urine reservoir 20 such that the urine reservoir 20 receives material excreted from the kidney equivalent 26. The nutrition reservoir 18, the faeces reservoir 19, and the urine reservoir 20 are integral parts of the antra layer 4 and are preferably configured to be externally accessible.

Figure 2:
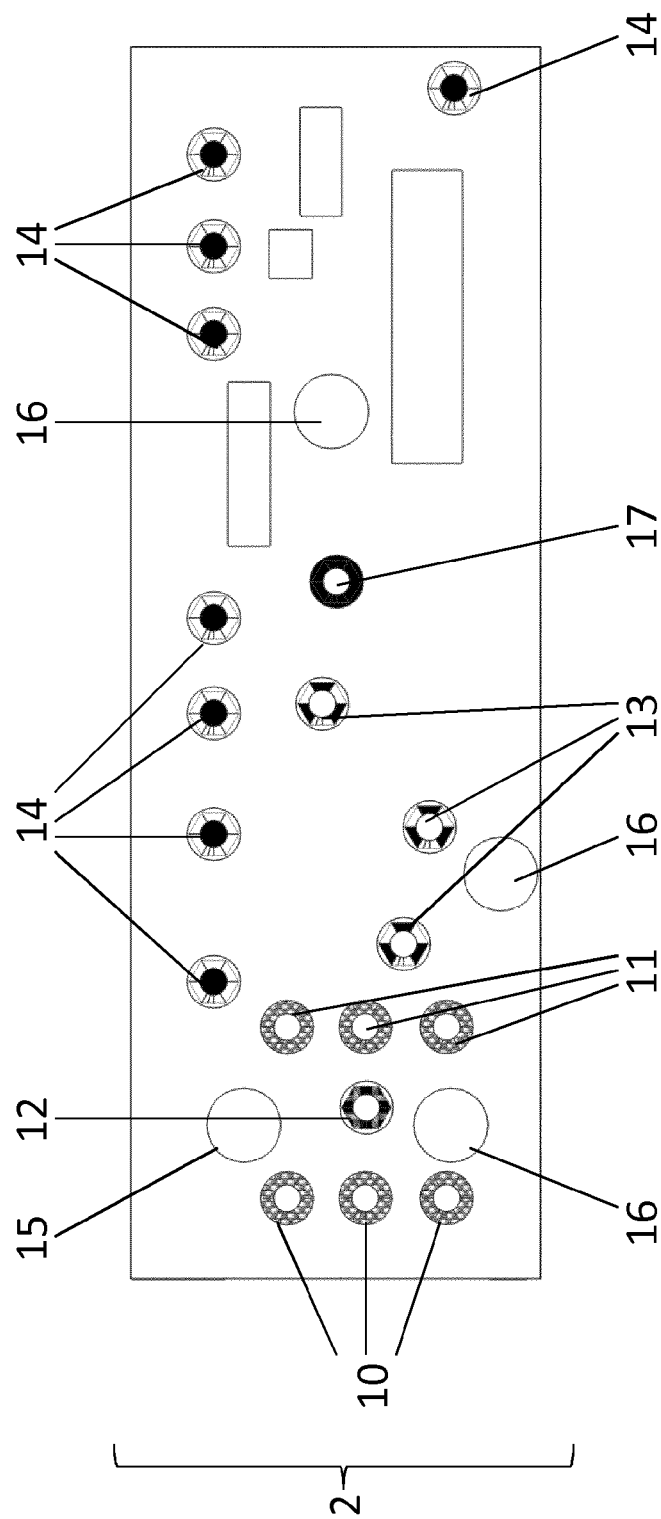
FIG. 2 shows a schematic top-down view on the actuator layer of the embodiment of FIG. 1.

The actuator layer 2 is configured to comprise a multiplicity of actuators arranged and configured to regulate a pressure force applicable on selected organ equivalents, the self-contained circulation system and/or part thereof, see FIG. 2. The actuator layer is made of polycarbonate.

The actuator layer 2 comprises:
- 3 pressure based actuators 10 acting on the self-contained circulation system 34 to allow for directed fluid movement in order to mimic heart beat;
- 3 peristaltic based actuators 11 acting on the antra layer 4 in such a way to allow for directed movement in order to mimic intestinal peristaltic movement;
- one actuator 12 acting on the lung equivalent 22 to allow for air-flow in order to mimic air breathing;
- one actuator 17 acting on the bone marrow equivalent 27 to allow for regulated compression in order to mimic bone compression;
- 8 actuators 14 acting on the arteriolar transport channel of the self-contained circulation system 34 in order to mimic arteriolar constriction;
- 1 actuator 13 acting on the liver equivalent 25 to allow for directed fluid movement in order to dissipate bile from the liver equivalent 25;
- 1 actuator 13 acting on the kidney equivalent 26 to allow for directed fluid movement in order to dissipate urine from the kidney equivalent 26 into the kidney reservoir 20; and
- 1 actuator 13 acting on the spleen equivalent 23.

Furthermore, the actuator layer comprises a port 16 to access the nutrition reservoir 18, a port 16 to access the feaces reservoir, a port 16 to access the urine reservoir 20 and one port 16 to access the venular transport channel of the self-contained circulation system 34.

Example 2

Integrating Biological Vasculature into a Multi-Organ-Chip Device of the Invention We aimed to emulate the transport part of the human vasculature—heart and vessels—on a chip in order to demonstrate feasibility of establishment of a functional vasculature equivalent on a multi-organ-chip or human-on-a-chip device of the invention. An on-chip micropump to support steady long-term fluid flow through a microchannel system fully covered by primary human dermal microvascular endothelial cells (HDMECs) was established. In contrast to the majority of the existing microsystems to investigate shear stress effects on ECs applying steady shear stress in the range of 10-40 dyn/cm$^2$, we aimed for pulsatile shear stress with reversing patterns which had been used earlier in different experimental settings. The microvascular transport system presented in this work interconnects two separate compartments which are designed for the integration of individual organ equivalents with a biomass capacity of up to 100 mg each. Special inserts were fabricated supporting vessel branching and diameter reduction in the areas of individual organ culture compartments to support later organ vascularization. Rapid prototyping applying soft lithography and replica moulding of PDMS allows the flexible adjustment of the design with regard to the number of organs and their specific arrangement, always adhering to the same standard chip basement format. Furthermore, two important features were implemented to overcome the technical handling restraints of the majority of existing microfluidic systems: i) incubator independent operation of the microsystem was assured by a tempered chip support, and ii) microscopic access to each and every area of the circuit channels was guaranteed, enabling real-time video microscopy.

Materials and Methods
Device Design and Fabrication

We designed and fabricated a microfluidic multi-organ-chip (MOC) device accommodating two separate microvascular circuits each operated by a separate peristaltic on-chip micropump. FIG. 7 illustrates the system at a glance. The cover-plate accommodates six air pressure fittings and four inserts forming 300 µl compartments, each for media exchange and later integration of organ equivalents. The MOC-holder supports controlled constant tempering of the MOC at 37° C. (FIG. 7a). Peristaltic on-chip micropumps (FIG. 7b) were installed. Micropump software control facilitates both clockwise and anti-clockwise fluid flow. The flow rate (Q) can be varied by the adjustment of the pumping frequency. Each microchannel circuit (FIG. 7c) comprises a total volume of 10 µl while the two individual insert-based compartments for further organ equivalent culture each have a volumetric capacity of up to 300 µl. Standard soft lithography and replica moulding of PDMS (Sylgard 184, Dow Corning, Midland, Mich., USA) has been applied for MOC fabrication. In brief, a master mould was fabricated by bonding of a silicon wafer to a glass wafer. Photoresist was applied to the silicon wafer and patterned by using a photomask and UV light. Subsequently unprotected silicon regions were etched and the photoresist was stripped. To fabricate the microsystem, the cover-plate (CP) was treated with a silicon rubber additive (WACKER® PRIMER G 790; Wacker Chemie, Munich, Germany) at 80° C. for 20 min. The prepared cover-plate was plugged to the master mould (channel height 100 µm, width 500 µm) and PDMS (10:1 v/v ratio of PDMS to curing agent) was injected into this casting station. The set-up was incubated at 80° C. for at least 60 min. Teflon screws were used to generate the four PDMS-free culture compartments and the six 500 µm thick PDMS membranes constituting the two on-chip micropumps (three membranes per micropump). The cast PDMS slice bonds fluid-tight to the CP. Thereafter, the PDMS slice attached to the CP was irreversibly bonded by low pressure plasma oxidation treatment (Femto; Diener, Ebhausen, Germany) to a microscope slide. Sterile medium was injected immediately into the two microvascular circuits to avoid surface neutralization.

Characterization of Fluid Dynamics

We applied non-invasive micro-particle image velocimetry (µPIV) to characterize the fluid flow in spot A and B (cf. FIG. 7c) of the microfluidic circuit. In brief, a Zeiss Primovert inverting microscope (Zeiss, Jena, Germany) with a standard halogen lamp as a continuous light-source, coupled to a CMOS-camera (Baumer Optronic HXC40, resolution: 2048×2048 pixel, interface: CameraLink; Baumer Optronic, Radeberg, Germany) was used to track the movement of 15 µm polystyrene beads (4*10$^4$ g/ml; Life Technologies, Darmstadt, Germany) at an exposure time of 4 µs per single image. A low magnification (4×) was chosen to constrain the shift between two frames to approximately 50 pixels (1 pixel=3.2 µm). The z-focus was set to the centre of the fluidic channel in the respective spot (50 µm above the glass slide) to detect the peak velocity. An interrogation window at the centre of the fluidic channel (1024 pixel×100 pixel, 3.28 mm×0.32 mm) was observed achieving frame rates up to 3200 fps. Finally, the correlation was carried out with a software programme (Fraunhofer IWS, Dresden, Germany) which analyses an image stack of 15,000 frames, calculating the correlation maximum for the x-component of the displacement in a specified area. The calculated values of five succeeding frames are averaged to minimize artefacts. The following pump configuration was used for all experiments: pressure—500 mbar; vacuum—520 mbar; and air flow—1.5 l/min at 350 mbar. The time-dependency was measured at two different places (A+B) on the chip, as shown in FIG. 7c.

As laminar flow has its velocity maximum ($v_{max}$) at the centre of the microchannel, the mean shear stress ($\tau$) can be calculated using the following equation:

$$\tau = \frac{-4\mu \cdot v_{max}}{h} \quad (1)$$

where $v_{max}$ is the magnitude of the averaged velocity at the centre of the channel, µ is the dynamic viscosity (calculated as 1 mPa/s) and h is the channel height (100 µm).

Cell Isolation and Culture

HDMECs were isolated from human foreskin obtained with informed consent and ethics approval from a paediatric surgery after routine circumcisions of juvenile donors. All skin samples used for cell isolation were processed within one day after their removal. Prior to isolation, the foreskins were cleaned in 80% ethanol for 30 s and rinsed with phosphate buffered saline (PBS; PAA, Coelbe, Germany). The skin-ring was opened and subcutaneous tissue was removed. In order to separate the thin epidermal layer from the dermis, the prepared foreskin was incubated in 5 mg/ml dispase II solution (Sigma-Aldrich, Schnelldorf, Germany) at 4° C. for 15-18 h. The dermis was cut into small pieces and then incubated with 4 mg/ml Collagenase NB 4 solution (Serva, Heidelberg, Germany) at 37° C. for 75 min. The mixture was passed through a 70 µm nylon filter and centrifuged at 300 g for 5 min. The resulting cell pellet was resuspended in Endothelial Cell Growth Medium MV2 (ECGM-MV2; PromoCell, Heidelberg, Germany) supplemented with Supplement-Pack MV2 (PromoCell, Heidelberg, Germany), 1% P-S and 0.05% fungizone. The cells were seeded into a T-75 flask and grown in 5% $CO_2$ at 37° C. The medium was replaced one day after seeding. Two to five days after the initial seeding, the HDMECs were purified by magnetic associated cell sorting (MACS). Cells were harvested using 0.05% (0.5 mg/ml) Trypsin/EDTA (PAA, Coelbe, Germany) and a positive selection for ECs using the CD31 MicroBead Kit (Miltenyi Biotec, Bergisch Gladbach, Germany) was performed according to the manufacturer's instructions. ECGM-MV2 supplemented with Supplement-Pack MV2 and 1% P-S (complete ECGM-MV2) was used to elude the cells from the column. A purity control of the isolated cells was performed directly after each MACS by FACS analyses. Where necessary, separation cycles were repeated until >90% of the cells were positive for CD31. The purified HDMECs were either frozen for later use or used immediately after expansion. HDMECs were expanded in T-75 flasks with complete ECGM-MV2 until 70-90% confluence at a three day feeding regimen. Cells between the 3rd and 8th passage were used for all studies to ensure that the cells retained their primary endothelial characteristics.

Culture of HDMEC on Different Treated PDMS Surfaces

HDMECs were seeded at a density of $10^4$ cells/cm$^2$ on three types of PDMS surfaces: untreated, coated with 100 μg/ml fibronectin (Sigma Aldrich, Schnelldorf, Germany) and treated with air plasma. Air plasma treatment was performed in a low pressure plasma system (50 W) at a frequency of 13.56 MHz for 30 s. After 48 h of cultivation, growth behavior and morphology of the cells was compared by light microscopy.

EC Seeding and Culture in the MOC

Prior to seeding, each MOC was flushed with medium and incubated statically for 3 days in 5% CO2 at 37° C. HDMECs were harvested from expansion cultures using 0.05% Trypsin/EDTA (PAA, Coelbe, Germany). The cell suspension was concentrated by centrifugation and cell counts were performed using the ViCell viability counter (Beckman Coulter, Fullerton, Calif., USA). Cell viability was >90% for all experiments. Centrifuged cells were resuspended with complete ECGM-MV2 to a final concentration of 2×10$^7$ cells/ml. Afterwards, the cell suspension was transferred to a 1 ml syringe. The cells were injected through one of the two compartments of each circuit. The syringe was connected to a female Luer x ¼-28 male adapter (IDEX Health & Science, Wertheim-Mondfeld, Germany). Air was pushed out of this fitting, which was then screwed to a special thread (MOC) adapter (MicCell MOC-I ¼"-28 UNF×M10 Fitting (PEEK); Gesim, Dresden, Germany). An empty syringe was connected in the same way to the second compartment. After even cell infusion into both circuits the device was incubated in 5% CO2 at 37° C. under static conditions for 3 h to allow the cells to attach to the channel walls. An amount of 300 μl fresh medium was added to each compartment and then flushed through the PDMS channels using the on-chip micropump of each circuit. A frequency of 0.476 Hz was applied to every microvascular circuit of the MOCs for continuous dynamic operation. For MOC cultures under static conditions, the channels were flushed with fresh medium for 5 min, utilising a difference in hydrostatic pressure between the inlet and outlet compartment.

An amount of 150 μl medium per compartment was replaced every 1-2 days in both dynamic and static MOC systems, and cell growth and viability were monitored by light microscopy inspection at spots A and B of each circulation (FIG. 7c). In addition, cell viability was determined with a Calcein AM assay. A solution of 5 μg/ml CellTrace calcein red-orange AM (Life Technologies, Darmstadt, Germany) was added into both compartments of each circuit of a MOC at a volume of 100 μl. The MOC was pumped for 2 min and then incubated under static conditions in 5% CO2 at 37° C. for 30 min. Thereafter, the microchannels were washed twice with medium by replacing the medium in the compartment inserts with fresh medium. Images were obtained using fluorescence microscopy (BZ9000; Keyence, Neu-Isenburg, Germany). Regular MOC experiments were finished after 4 days (10 dynamic MOCs and 12 static MOCs). Individual MOCs were operated at the same mode over 7, 14 and 32 days to gain first indications on long term performance of the microvascular circuits. In order to evaluate the possibility of replacing the CO2-incubator for MOC operation by the MOC-holder shown in FIG. 7a, 9 MOC experiments (7 dynamic MOCs and 2 static MOCs) were performed using the holder exclusively for operation times of up to 7 days.

Characterization of EC Metabolism in the MOC

Glucose concentration of the medium was measured, according to the manufacturer's instructions, using the Stanbio Glucose LiquiColor® (Oxidase) Procedure No. 1070 (Stanbio Laboratory, Boerne, Tex., USA). Briefly, 99 μl of the reagent were added to a 96 microtitre plate (Greiner Bio-One, Frickenhausen, Germany) prewarmed to 37° C. and 1 μl of medium sample was added. After another 5 min of incubation at 37° C., the glucose concentration was quantified in a microplate reader (FLUOstar Omega; BMG Labtech, Ortenberg, Germany) at 500 nm, using water as a reference.

Lactate concentration of the medium was measured, according to the manufacturer's instructions, using the LOD-PAP Method (Diaglobal, Berlin, Germany). Briefly, 99 μl of the reagent was mixed with 1 μl of medium sample in a 96-well format multiwell plate and absorbance was measured at 520 nm in a microplate reader, using water as a reference.

Immunofluorescence Staining of ECs Inside the MOC

After 4 days in culture, the ECs were fixed inside the microvascular circuit with cold acetone at −20° C. for 10 min, rinsed twice with PBS for 5 min, incubated with 10% goat serum in PBS for another 20 min, and then incubated with the primary antibody, mouse anti-human CD31 (1:500; 7.1 mg/ml; DRFZ, Berlin, Germany), at room temperature (RT) for 2 h. Subsequently, the circuits were washed twice with PBS followed by incubation with the secondary antibody, Alexa Fluor 594 goat anti-mouse (1:200, 2 mg/ml; Life Technologies, Darmstadt, Germany), in the dark at RT for 40 min After washing, the antibody sheep anti-human vWF-FITC (1:50, 10 mg/ml; Abcam, Cambridge, UK) was added and incubated at RT for 2 h. Nuclei were counterstained with Hoechst 33342 (1:1000, 10 mg/ml; Life Technologies, Darmstadt, Germany). Another immunofluorescence staining with the primary antibody mouse anti-human VE-Cadherin (1:100, 0.2 mg/ml; Santa Cruz Biotechnology, Heidelberg, Germany) was carried out: ECs were fixed with 4% PFA for 10 min, rinsed twice with PBS for 5 min and permeabilised with 0.2% Triton X-100 for 5 min. After washing twice with PBS, staining for primary and secondary antibodies was performed, as described above. MOC cultures were stained for filamentous actin with Oregon Green® 488 phalloidin (Life Technologies, Darmstadt, Germany), according to the manufacturer's instructions, in combination with VE-Cadherin.

Each solvent was added to the compartment inserts of the MOC and pumped for 1-2 min for even distribution. Images were taken either by standard fluorescence microscopy or two-photon microscopy (TriMScope II; LaVision BioTec, Bielefeld, Germany). All microvascular channels were imaged through their microscope slide wall. 3D images were reconstructed from the image stack collected, using Imaris software (Bitplane, Zurich, Switzerland).

Characterization of Shear Stress Effects

Images of immunofluorescence stained HDMECs were taken at spots A and B of each microvascular circuit (FIG. 7c) to monitor flow-induced morphological changes using a standard fluorescence microscope. HDMEC membranes on the images were retraced manually for automatic EC recognition. A connected area recognition algorithm was used to identify the ECs and calculate the corresponding perimeter, cell size, centre of gravity, and orientation (spatial unweighted second moment's main axis) of each EC. A non-dimensional shape index (SI) parameter was used to quantify cell elongation that is defined as:

$$SI = \frac{4 \Pi A}{P^2} \quad (2)$$

where A is the area of the cell and P is the perimeter of the cell. The SI ranges from 0 to 1, where 0 is a straight line and 1 is a perfect circle. Additionally, the angle of orientation was measured to quantify the alignment of HDMECs in the flow direction where 0° is a cell's main axis aligned perfectly with the direction of flow and 90° is a cell aligned orthogonal to the direction of flow. The source code was implemented in Matlab (MathWorks, Ismaning, Germany). The SI and cell orientation angle for at least 200 cells per image were used for analysis.

Generation of Microchannels Structured by Femtosecond Laser Ablation

A CAM-guided femtosecond laser (TissueSurgeon; Rowiak, Hannover, Germany) with a wavelength of 1030 nm (pulse energy=120 nJ), a pulse duration of 400 fs and a repetition rate of 10 MHz was used by Rowiak to generate microchannels as low as 40×40 μm$^2$ into the PDMS material. The channel design was chosen to reveal minimal achievable diameters and to allow continuous media flow through each of the branched channels. HDMECs were seeded into pre-structured microchannels within a PDMS mould and stained with Calcein AM assay (Life Technologies, Darmstadt, Germany) after 1 day of cultivation. Afterwards, the PDMS mould was placed into the tissue compartment of the MOC. Images were acquired by standard fluorescence microscopy.

Results and Discussion

Evaluation of Fluid Dynamics

We successfully applied μPIV to exemplarily characterize fluid flow profiles at different spots of the MOC circuits (FIG. 8a). Thorough microscopic access to each and every area of the MOC facilitates in-depth analyses of various other regions of the MOC and variable MOC designs in the future. The potential for optimal analysis by microscopy and the operational modus of the peristaltic micropump membranes of a microfluidic MOC circuit filled with human red blood cells from a worm's-eye view could be demonstrated. A robust peristaltic on-chip micropump has been integrated into a microvascular circuit capable of faultlessly circulating media at sterile conditions over weeks and months at a flow rate ranging from 7 μl/min (lowest frequency) to 70 μl/min (highest frequency). The frequency of pulsatile operation can be increased up to 2.4 Hz, which corresponds to a high but still physiological heart activity of 144 beats per minute in humans. At this frequency, the shear stress measured at spots A and B of the microvascular circuit reaches approximately 25 dyn/cm$^2$ (FIG. 8b), which is a physiological shear stress at the higher end of the scale in microvasculature. The mean velocity increased almost linearly with the pumping frequency. The pumping frequency used in our experiments (0.476 Hz) corresponds to less than 30 "heart-beats" per minute (approximately half of the physiological value of an adult at rest) to avoid EC loss during early phases of surface coverage. This phase somehow resembles elements of wound healing in vivo. As illustrated in FIG. 8a, oscillatory shear stress—another desired physiological feature—could be implemented into MOC operation through the micropump design. The waveform of such oscillation at a certain local position in the microvasculature depends upon the pumping frequency and the particular design of a MOC. Certain waveforms in humans have been associated with certain disease susceptibility. This implies the further evaluation of the MOC platform for research into such pathological processes of the human cardiovascular system.

EC Source, Isolation and Culture

As of today, the majority of human EC shear stress research in microfluidic systems is carried out on human umbilical vein endothelial cells (HUVECs) due to easy access to large cell numbers and their high phenotype pliability. We hypothesize that HDMECs own at least the same pliability of phenotype, but with a higher potential of rapid in vitro adaptation toward changing local environment. Kamm and co-workers, for example, succeeded in culturing HDMECs in a vertical plane of microchannels and monitor capillary morphogenesis into collagen gels in the lateral plane. In contrast to all other organs of the body, skin in vertebrates needs to adapt rapidly to eventually changing external temperatures by immediate blood vessel contraction or relaxation. Moreover, skin of carnivores is the organ with the most pronounced exposure to repeated injury, due to their aggressive life-style. These two factors taken together with human longevity might have selected HDMECs for an unmatched pliability of their phenotype and a unique potential for neoangiogenesis. Both factors are of outmost importance for the establishment of a functional in vitro equivalent to human vasculature. The capacity for neoangiogenesis, in particular, is crucial for the establishment of the second part of human vasculature—the capillary network of organ equivalents—in MOCs. The latest discoveries in molecular mechanisms of angiogenesis underpin the essential role of local environment including shear stress. Various techniques have been described to isolate human ECs from different tissues. The magnetic bead isolation of ECs after tissue digestion with CD31 (PECAM-1) Micro-Beads was applied because it is constitutively expressed at the surface of virtually all types of ECs and is not present on any other cell type apart from the white blood cell population. In particular, it is not expressed on dermal fibroblasts and smooth muscle cells. Morphology and several endothelial-specific markers were examined to confirm the endothelial origin. The isolated HDMECs showed cobblestone-like morphology in phase contrast and were positive for the endothelial-specific marker CD31, VE-Cadherin and von Willebrand Factor (vWF). Staining for 5B5, a fibroblast-specific marker, and α-smooth muscle-actin, a smooth muscle cell-specific marker, showed no outgrowth of other cell types. In addition, HDMECs showed an uptake of Alexa594-labeled ac-LDL after 4 h of exposure. A mix of dermal fibroblasts and smooth muscle cells served as the control for all stainings (data not shown). HDMECs could be cultured for up to eight passages without significant changes in morphology and marker expression. Our data indicate that this method is a robust and reproducible way to isolate CD-31 positive HDMECs from human foreskin. The average number of HDMECs fully covering two microvascular circuits of a MOC was calculated to be in the range of 2*105 cells. On average, 1*107 primary HDMECs after sorting can be prepared from a single human foreskin. A cell amplification factor of ~3000 holds true between initial seeding and passage 7-8 of HDMEC culture, thus enabling the provision of 3*1010 cells from a single foreskin. Theoretically, this is equivalent to 5000 cell-loaded MOCs (two circuits per MOC). Optimization of preparation and propagation might be envisioned to further improve the HDMEC yield.

Establishment of Stable Microvascular Circuits in the MOC

A pilot comparison study between EC attachment to fibronectin-coated and air plasma-treated PDMS surfaces revealed an at least equal adherence of HDMECs to PDMS in static cultures. In addition, plasma treatment has long been recognized as a viable technique to increase hydrophilicity of PDMS microchannels. Therefore, air plasma treatment was finally chosen for surface activation during the fabrication of MOCs. Fibronectin is widely used as a coating material for EC attachment and cultivation in PDMS-based microfluidic devices. Although easy to handle at laboratory research scale, a fibronectin coating procedure may hamper process speed and sterility at later large industrial scale at high throughput. PDMS treatment with air plasma in our hands is a reproducible, fast and scalable method to prepare PDMS-based microdevices for efficient EC attachment.

Thereafter, a microvascular circuit comprising a peristaltic micropump, two compartments for later organ equivalent cultures and connecting microchannels, entirely covered with a functional HDMEC monolayer, has been established in a pulsatile media flow within 4 days of culture. We earlier demonstrated full circuit coverage with a human EC line elsewhere. Here, we focused on the rapid establishment of such a miniaturized human cardiovascular transport system based on primary HDMECs. In addition, daily tracking of the metabolic activity of ECs was performed. The increased metabolic activity within the first days of surface attachment and coverage can be explained by increased motility and proliferation of cells. A system attrition rate of 50% in the early stages of experiments, primarily caused by contaminations, has now been efficiently reduced to about 20% during routine MOC use in our laboratory. Total quality management systems installed in each and every industrial in vitro testing laboratory might fully eliminate this "research lab" attrition rate. ECs maintained adherence to the channel walls and remained viable, as seen by Calcein AM red orange staining. In addition, cells were tested for the uptake of Alexa594-ac-LDL. As no further change in endothelial morphology had been observed after 4 days of cultivation, the experiments were stopped for analysis. In-depth immunofluorescence analyses of the tight EC layer at day 4 revealed striking viability and vascular functionality. The HDMECs forming the microvascular circuit were positive for CD31, vWF and VE-Cadherin. Furthermore, HDMECs were able to cover all walls of the channels forming a fluid-tight layer. Such stable microvascular circuits, on the one hand, might act as biological membranes preventing the transfer of molecules into the surrounding PDMS slice described recently. On the other hand, they might serve as haemocompatible vessel networks for whole blood circulation, preventing blood clotting.

Impact of Shear Stress

When exposed to laminar shear stress, ECs align themselves and their microfilaments in the direction of the flow. In vivo ECs in different locations are exposed to different types of flow, such as laminar, pulsatile and turbulent; the latter, for example, has been described to increase turnover. Physiological shear stress-induced elongation and flow alignment was evidenced in our MOC cultures plotting the SI and angle of orientation of HDMECs in the microvascular circuits generated at pulsatile flow (Q=40.56 µl/min, τ=5.17 dyn/cm$^2$), against those generated under static culture conditions. A change in the distribution of filamentous actin (F-actin) was observed between static and dynamic cultivation. ECs in static conditions are polygonal and F-actin is organised as a dense band in the periphery of the cell; meanwhile at shear stress of about 5 dyn/cm$^2$, F-actin creates bundles of stress fibres. SI and angle of orientation differed significantly between static and dynamic cultivation of ECs in the MOC, and were in the range of previous findings for HDMECs in microfluidic devices.

Finally, we observed equally outstanding cell viability at spots of analysis in a limited number of indicative long-term experiments with microvascular MOCs over 14 days (n=4) of culture and in a first single microvascular MOC over 32 days (data not shown).

CONCLUSION

We hypothesize that blood circulation through EC-lined microcircuits connecting organ equivalents with each other in a physiological order is the first and prime essential requirement to fully emulate human organismal homeostasis at microscale. Therefore, we here successfully applied soft lithography, replica moulding and two-photon laser ablation techniques to establish an incubator independent microvascular circulation system mimicking the transport function of the human cardiovascular system at microscale. It is arranged in a two-layer glass-PDMS chip the area of a standard microscopic slide, with channel heights of 100 µm and a total height of 3 mm. Two separate cylindrical tissue culture inserts, each the area of a standard cavity of a 96-well plate, are positioned in the microvascular circuit. A robust 4 day procedure applying pulsatile shear stress has been established to cover all fluid contact surfaces of the system with a functional, tightly closed layer of HDMECs. In contrast to the vertical plane HDMEC growth described in literature the entire coverage of our microvascular system with human ECs render possible biological haemocompatibility of such a microvascular system for the first time. The chip layout reduces the circulating fluid volume in the microvascular transport system down to 10 µl, at least two magnitudes lower than the circulation volume applied in any of the systems operated with external pumps and reservoirs. More important tissue culture inserts, each of a maximum volume of 300 µl, will allow for the exact adjustment of physiological fluid-to-tissue ratios once individual organ equivalents are established in the next development step. The fabrication technique is convenient and versatile, and design changes can be implemented in design-to-device turnaround times of only 2-3 months. The alignment and elongation of ECs in the direction of flow, thoroughly demonstrated in vitro, has been monitored in perfect detail through time-lapse video microscopy. Other microfluidic channel designs have been equally efficiently covered with HDMECs in our laboratories by the technique described. We have generated first indications that once a microvascular circulation system is established, it eventually has an operating life of at least 32 days.

LIST OF REFERENCE NUMBERS 1 multi-organ-chip device
2 actuator layer
3 base layer
4 antra layer
5 organ-holder layer
6 organ layer
10 pressure based actuator (heart)
11 peristaltic based actuator
12 air-flow actuator
13 actuators
14 arteriolar constriction actuator
16 port
17 bone-compression actuator
18 nutrition reservoir
19 faeces reservoir
20 urine reservoir
21 small intestine equivalent
22 lung equivalent
23 spleen equivalent
24 pancreas equivalent
25 liver equivalent
26 kidney equivalent
27 bone marrow equivalent
28 adipose tissue equivalent
29 brain equivalent
30 testes equivalent
31 skin equivalent
32 electric sensor
33 sensor
34 self-contained circulation system

The invention claimed is:

1. Multi-organ-chip device comprising
a base layer;
an organ layer arranged on the base layer;
an organ-holder layer arranged on the organ layer:
an antra layer arranged on the organ-holder layer; and
an actuator layer arranged on the antra layer;
wherein
the base layer is configured to provide a solid support for the further layers;
the organ layer is configured to comprise
a multiplicity of individual organ equivalents, each organ equivalent comprising at least one organ growth section, each organ growth sections including an organoid cavity for housing at least one organoid of an organ, and a micro-inlet and a micro-outlet for fluid communication between the organoid cavity and a self-contained circulation system, wherein the organ layer includes at least one organ equivalent configured to represent one of the following organs lungs, small intestine, spleen, pancreas, liver, kidneys, and bone marrow, respectively, and
the self-contained circulation system is configured to be in direct fluid communication with the organ growth sections of the organ layer via the micro-inlets and micro-outlets of the organ growth sections;
the antra layer is configured to comprise a multiplicity of cavities and tubes arranged to be in fluid communication with selected organ equivalents or organ growth sections allowing for an exchange of fluids between cavities and organ growth sections;
the organ-holder layer configured to seal and stabilize the organ layer and maintain fluid communications between the multiplicity of individual organ equivalents and the antra layer; and
the actuator layer is configured to comprise a multiplicity of actuators arranged and configured to regulate a pressure force applicable on a selected organ equivalent and the self-contained circulation system.

2. The multi-organ-chip device of claim 1, wherein the base layer is made of a transparent material.

3. The multi-organ-chip device of claim 2, wherein the base layer includes glass or a transparent synthetic polymer.

4. The multi-organ-chip device of claim 1, wherein the base layer comprises at least one sensor configured to measure signals emitted from and to transmit signals to one or more of the organ equivalents and the organ growth sections, and from the self-contained circulation system.

5. The multi-organ-chip device of claim 1 comprising an organ equivalent configured to represent the lungs, wherein the self-contained circulation system comprises
an arteriolar transport channel directly connecting the micro-outlets of the organ growth sections of the lung equivalent with the micro-inlets of all organ growth sections of the organ layer for transport of fluid with high $pO_2$ to organ growth sections; and
a venular transport channel directly connecting the micro-outlets of the organ growth sections with the micro inlets of the organ growth sections of the lung equivalent for transport of fluid with low $pO2$ from the organ growth sections to the lung equivalent.

6. The multi-organ-chip device of claim 5 further comprising organ equivalents configured to represent the small intestine, the spleen, and the pancreas, wherein the self-contained circulation system is configured such that the micro-outlets of the organ growth sections of small intestine, spleen, and pancreas equivalents are connected to be in direct fluid communication with each other and with additional micro-inlets of the organ growth sections of the liver equivalent for fluid communication between the spleen, pancreas, small intestine, and liver equivalents, wherein fluid communication from the spleen, pancreas, and small intestine towards the venular transport channel of the self-contained circulation system occurs via passage through the liver equivalent.

7. The micro-organ-chip device of claim 5, wherein the multiplicity of individual organ equivalents further includes: skin, testes, brain, adipose tissue, and combinations thereof.

8. The multi-organ-chip device of claim 5, further comprising organ equivalents representing the small intestine, the spleen, the pancreas, the liver, the kidney, and the bone marrow, respectively, wherein the arteriolar transport channel originating from the lung equivalent includes, in a direction of flow:
a first bifurcation at which a first arteriolar channel branches off and supplies the small intestine, the spleen, and the pancreas equivalents;
a second bifurcation at which a second arteriolar channel branches off and supplies the liver equivalent;
a third bifurcation at which a third arteriolar channel branches off and supplies the kidney equivalent; and
a fourth bifurcation at which a fourth arteriolar channel branches off and supplies the bone marrow.

9. The multi-organ-chip device of claim 8, wherein a diameter of the arteriolar transport channel in the flow direction is constantly reduced and a sum of cross-sectional areas of all arteriolar transport channels, including all bifurcations at a given distance from the lung equivalent, remains constant; and in the venular transport channel the reduction in diameter is constantly reverted in the flow direction and a sum of cross-sectional areas of all venular transport channels, including all bifurcations at a given distance from the lung equivalent, remains constant.

10. The multi-organ-chip device of claim 7, further comprising organ equivalents representing the small intestine, the spleen, the pancreas, the liver, the kidney, the bone marrow, the skin, the testes, the brain, and the adipose tissue, respectively, wherein the arteriolar transport channel originating from the lung equivalent includes:
    a first bifurcation at which a first arteriolar channel branches off and supplies the small intestine, the spleen, and the pancreas equivalents;
    a second bifurcation at which a second arteriolar channel is branches off and supplies the liver equivalent;
    a third bifurcation at which a third arteriolar channel is branches off and supplies the kidney equivalent;
    a fourth bifurcation at which a fourth arteriolar channel branches off and supplies the bone marrow;
    a fifth bifurcation at which a fifth arteriolar channel branches off and supplies the skin equivalent;
    a sixth bifurcation at which a sixth arteriolar channel branches off and supplies the adipose tissue equivalent;
    a seventh bifurcation at which a seventh arteriolar channel branches off and supplies the testes equivalent; and
    an eighth bifurcation at which an eighth arteriolar channel branches off and supplies the brain equivalent.

11. The multi-organ-chip device of claim 10, wherein a diameter of the arteriolar transport channel in the flow direction is constantly reduced and a sum of cross-sectional areas of all arteriolar transport channels, including all bifurcations at a given distance from the lung equivalent, remains constant; and in the venular transport channel the reduction in diameter is constantly reverted in the flow direction and a sum of cross-sectional areas of all venular transport channels, including all bifurcations at a given distance from the lung equivalent, remains constant.

12. The multi-organ-chip device of claim 1 comprising organ equivalents configured to represent the small intestine, the liver, and the kidney, wherein the antra layer is configured to comprise:
    a first cavity located on top of the small intestine equivalent and in fluid communication with the small intestine equivalent and a nutrition reservoir, wherein the small intestine equivalent is supplied with nutrients from the nutrition reservoir;
    a second cavity located on top of the small intestine equivalent and in fluid communication with the small intestine equivalent and a faeces reservoir, wherein material excreted from the small intestine equivalent can be transported to the faeces reservoir via the second cavity;
    a third cavity located on top of the liver equivalent and in fluid communication with both the liver equivalent and the second cavity, wherein material excreted from the liver equivalent can be transported to the feces reservoir via the second cavity; and
    a fourth cavity located on top of the kidney equivalent and in fluid communication with the kidney equivalent and a urine reservoir, wherein the urine reservoir receives material excreted from the kidney equivalent via the fourth cavity.

13. The multi-organ-chip device of claim 1, comprising organ equivalents configured to represent the lungs, the small intestine, the spleen, the river, the kidneys, and the bone marrow, respectively, wherein the actuator layer comprises:
    one or more actuators configured to act on the self-contained circulation system to direct fluid movement to mimic heart beat;
    one or more actuators configured to act on the antra layer to direct movement to mimic intestinal peristaltic movement;
    one or more actuators configured to act on the lung equivalent to direct air to mimic breathing;
    one or more actuators configured to act on the bone marrow equivalent to regulate compression to mimic bone compression;
    one or more actuators configured to act on the arteriolar transport channel of the self-contained circulation system to mimic arteriolar constriction;
    one or more actuators configured to act on the liver equivalent to direct fluid movement to dissipate bile from the liver equivalent; and
    one or more actuators configured to act on the antra layer to direct fluid movement to dissipate urine from the kidney equivalent.

14. The multi-organ-chip device of claim 1, wherein the organ layer includes:
    a liver equivalent having an organ growth section including an organoid cavity configured to house 5 to 15 liver organoids, wherein each liver organoid is a liver lobulus;
    a lung equivalent having an organ growth section including an organoid cavity configured to house 2000 to 4000 lung organoids, wherein each lung organoid is a lung alveola;
    a pancreas equivalent having an organ growth section including an organoid cavity configured to house 5 to 15 pancreas organoids, wherein each pancreas organoid is a Langerhans' isle;
    a spleen equivalent having an organ growth section including an organoid cavity configured to house 5 to 15 spleen organoids, wherein each spleen organoid is a white and red pulpa;
    a small intestine equivalent having an organ growth section including an organoid cavity configured to house 40 to 80 small intestine organoids, wherein each small intestine organoid is a villus;
    a kidney equivalent having an organ growth section including an organoid cavity configured to house 10 to 30 kidney organoids, wherein each kidney organoid is a nephron; and
    a bone marrow equivalent having an organ growth section including an organoid cavity configured to house 1000 to 2000 bone marrow organoids, wherein each bone marrow organoid is a unit formed of bone marrow, bone, and cartilage.

15. The multi-organ-chip device of claim 14, wherein
    the organoid cavity of the liver equivalent is configured to house 10 liver organoids;
    the organoid cavity of the lung equivalent is configured to house 3000 lung organoids;
    the organoid cavity of the pancreas equivalent is configured to house 10 pancreas organoids;
    the organoid cavity of the spleen equivalent is configured to house 10 spleen organoids;
    the organoid cavity of the small intestine equivalent is configured to house 60 small intestine organoids;

the organoid cavity of the kidney equivalent is configured to house 20 kidney organoids; and the organoid cavity of the bone marrow equivalent is configured to house 1400 bone marrow organoids.

16. The multi-organ-chip device of claim 1, wherein the organ layer includes:
- a skin equivalent having an organ growth section including an organoid cavity for housing 10 to 15 skin organoids, wherein each skin organoid is a skin appendix;
- a adipose tissue equivalent having an organ growth section including an organoid cavity for housing 200.000 to 300.000 adipose tissue organoids, wherein each adipose tissue organoid is an adipose cluster;
- a testes equivalent having an organ growth section including an organoid cavity for housing 10 to 20 testes organoids, wherein each testes organoid is a testes follicle; and
- a brain equivalent having an organ growth section including an organoid cavity for housing 150 to 250 brain organoids, wherein each brain organoid is a cerebral cortex column.

17. The multi-organ-chip device of claim 16, wherein
the organoid cavity of the skin equivalent is configured to house 15 skin organoids;
the organoid cavity of the adipose tissue equivalent is configured to house 240.000 adipose tissue organoids;
the organoid cavity of the testes equivalent is configured to house 15 testes organoids; and
the organoid cavity of the brain equivalent is configured to house 200 brain organoids.

18. The multi-organ-chip device of claim 1, wherein the base layer includes glass, the organ layer includes polydimethylsiloxane (PDMS), the organ-holder layer includes polycarbonate, the antra layer includes PDMS, and the actuator layer includes polycarbonate.

19. The multi-organ-chip device of claim 1, wherein the organ equivalents are each configured to house a predetermined number of organoids proportional to a number of organoids present in average in the selected organ of a mammalian organism, and all organ equivalents of the multi-organ-chip device are reduced in size by the same predetermined proportionality factor.

* * * * *